US007644722B2

(12) United States Patent
Christensen et al.

(10) Patent No.: US 7,644,722 B2
(45) Date of Patent: Jan. 12, 2010

(54) MEDICAL VALVE AND METHOD TO MONITOR INTRA-ABDOMINAL PRESSURE

(75) Inventors: Mark A. Christensen, Salt Lake City, UT (US); Timothy R. Wolfe, Salt Lake City, UT (US); Perry W. Croll, Salt Lake City, UT (US); Marshall T. Denton, Salt Lake City, UT (US); Edward J. Kimball, Salt Lake City, UT (US)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 547 days.

(21) Appl. No.: 11/199,790

(22) Filed: Aug. 9, 2005

(65) Prior Publication Data

US 2007/0038143 A1 Feb. 15, 2007

Related U.S. Application Data

(63) Continuation-in-part of application No. PCT/US04/06409, filed on Mar. 1, 2004, which is a continuation-in-part of application No. 10/379,222, filed on Mar. 4, 2003, now Pat. No. 7,112,177.

(51) Int. Cl.
*G05D 7/00* (2006.01)
*G05D 9/00* (2006.01)
(52) U.S. Cl. .......................... 137/107; 251/33; 251/45
(58) Field of Classification Search ................ 251/45, 251/33; 137/107
See application file for complete search history.

(56) References Cited

U.S. PATENT DOCUMENTS

| 1,600,793 A | 9/1926 | Bogan |
| 1,666,332 A | 4/1928 | Hirsch |
| 1,712,848 A | 5/1929 | Rose |

(Continued)

FOREIGN PATENT DOCUMENTS

| EP | 0 258 690 | 8/1987 |
| WO | WO 2004/078235 | 9/2004 |
| WO | WO 2004/080519 A1 | 9/2004 |

OTHER PUBLICATIONS

Fusco et al., "Estimation of Intra-abdominal Pressure by Bladder Pressure Measurement: Validity and Methodology," The Journal of Trauma® Injury, Infection, and Critical Care, Feb. 2001, pp. 297-302, vol. 50, No. 2.

(Continued)

*Primary Examiner*—John K Fristoe, Jr.
(74) *Attorney, Agent, or Firm*—TraskBritt

(57) ABSTRACT

An apparatus for monitoring the intra-abdominal pressure of a hospitalized patient includes a urinary catheter connected to a urine valve providing selectable communication between a discharge end of the urinary catheter and either a drain or a fluid source. Preferably, the urine valve is adapted for remote actuatation and has a housing adapted to resist patient discomfort from leg-valve contact. Plumbing structure desirably maintains fluid supply and drain conduits in a substantially parallel arrangement to assist routing those conduits between a patient's legs. When the urine valve is oriented to permit communication with the fluid source, an infusion pump may be used to infuse a known quantity of fluid through the urine valve and into the patient's bladder. A pressure transducer desirably is connected in-circuit to indicate the fluid's pressure. To facilitate the infusion process, an automatic flow control device may be included in a fluid supply path and arranged to permit repetitive operation of a syringe to inject a bolus of fluid into the patient's bladder. Subsequent to a period of time in which to make a pressure measurement, preferred embodiments of the urine valve automatically return to a bladder draining position.

13 Claims, 15 Drawing Sheets

U.S. PATENT DOCUMENTS

| | | | |
|---|---|---|---|
| 3,100,490 A | | 8/1963 | Robert |
| 3,103,229 A | * | 9/1963 | Smith .......................... 137/107 |
| 3,620,255 A | | 11/1971 | Stillman |
| 3,674,052 A | | 7/1972 | Hartman et al. |
| 3,794,043 A | | 2/1974 | McGinnis |
| 4,210,173 A | | 7/1980 | Choski et al. |
| 4,217,911 A | | 8/1980 | Layton |
| 4,301,811 A | | 11/1981 | Layton |
| 4,538,621 A | | 9/1985 | Jarczyn |
| 4,705,073 A | | 11/1987 | Beck |
| 4,966,161 A | | 10/1990 | Wallace et al. |
| 5,207,641 A | | 5/1993 | Allton |
| 5,385,563 A | | 1/1995 | Gross |
| 5,433,216 A | | 7/1995 | Sugrue et al. |
| 5,647,845 A | | 7/1997 | Haber et al. |
| 5,713,850 A | | 2/1998 | Heilmann et al. |
| 5,865,764 A | | 2/1999 | Moorhead |
| 5,899,434 A | * | 5/1999 | Nishimura ............... 251/30.02 |
| 5,916,153 A | | 6/1999 | Rhea |
| 5,916,230 A | | 6/1999 | Brenneman et al. |
| 6,102,888 A | | 8/2000 | Walker |
| 6,287,265 B1 | | 9/2001 | Gleason |
| 6,334,064 B1 | | 12/2001 | Fiddian-Green |
| 6,382,001 B1 | | 5/2002 | Neeley et al. |
| 6,434,418 B1 | | 8/2002 | Neal et al. |
| 6,447,462 B1 | | 9/2002 | Wallace et al. |
| 6,494,208 B1 | | 12/2002 | Morejon |
| 6,503,208 B1 | | 1/2003 | Skovlund |
| 6,877,714 B2 | * | 4/2005 | Hall ............................ 251/45 |
| 7,097,632 B2 | | 8/2006 | Shia et al. |
| 7,112,177 B2 | | 9/2006 | Christensen et al. |
| 7,381,190 B2 | | 6/2008 | Sugrue et al. |
| 2002/0065472 A1 | | 5/2002 | Brockway et al. |
| 2002/0082610 A1 | | 6/2002 | Cioanta et al. |
| 2002/0115966 A1 | | 8/2002 | Christensen et al. |
| 2003/0062281 A1 | | 4/2003 | Giard et al. |
| 2003/0195478 A1 | | 10/2003 | Russo |
| 2004/0082909 A1 | | 4/2004 | Shia et al. |
| 2006/0079804 A1 | | 4/2006 | Sugrue et al. |

OTHER PUBLICATIONS

Kirkpatrick et al., "Is Clinical Examination an Accurate Indicator of Raised Intra-abdominal Pressure in Critically Injured Patients?" CJS, Jun. 2000, pp. 207-211, vol. 43, No. 3.

Lozen et al., "Intraabdominal Hypertension and Abdominal Compartment Syndrome in Trauma: Pathophysiology and Interventions," AACN Clinical Issues: Advanced Practice in Acute Critical Care, Feb. 1999, pp. 104-112, vol. 10, No. 1.

Malbrain et al., "Abdominal pressure in the critically ill: measurement and clinical relevance," Intensive Care Med, 1999, pp. 1453-1458, vol. 25.

Sugrue et al., "Intra-abdominal pressure: time for clinical practice guidelines?" Intensive Care Med, 2002, pp. 389-391, vol. 28.

International Preliminary Report on Patentability. PCT/US2004/033463, dated Apr. 11, 2007.

Partial European Search Report for EP 04 79 4734 dated May 29, 2009.

PCT International Search Report, PCT/AU2004/000282, dated Apr. 28, 2004.

PCT International Search Report, PCT/US04/06409, dated Dec. 26, 2006.

PCT Written Opinion. PCT/AU2004/000282, dated Apr. 28. 2004.

Office Action for U.S. Appl. No. 11/825,215, dated Dec. 16, 2008.

Office Action for U.S. Appl. No. 11/219,319, dated Jul. 10, 2009.

Cheatham et al., Intraabdominal Pressure: a Revised Method for Measurement. 1997, pp. 594-595, Elsevier Science Inc.

Burch et al., Abstract, the abdominal compartment syndrome. Surg. Clin. North Am., 1996, pp. 833-842, vol. 76.

Kron et al., The measurement of intra-abdominal pressure as a criterion for abdominal re-exploration, Ann. Surg., 1984, pp. 28-30. vol. 199.

Iberti et al., Abstract, A simple technique to accurately determine intra-abdominal pressure, Crit. Care Med., 1987, pp. 1140-1142, vol. 15.

Iberti et al., Abstract, Determination of intra-abdominal pressure using a transurethral bladder catheter: clinical validation of the technique, Anesthesiology, 1989, pp. 47-50. vol. 70.

Platt et al., Abstract. Mortality associated with nosocomial urinary-tract infection, N. Eng. J. Med., 1982, pp. 637-642, vol. 307.

U.S. Appl. No. 11/665,133, filed Apr. 11, 2007, Christensen et al., Intra-Abdominal Pressure Monitoring Device and Method.

U.S. Appl. No. 11/825,215, filed Jul. 3, 2007, Christensen et al., Apparatus For Monitoring Intra-Abdominal Pressure.

* cited by examiner

MEDICAL VALVE AND METHOD TO MONITOR INTRA-ABDOMINAL PRESSURE

CROSS-REFERENCE TO RELATED APPLICATION(S)

This patent application is a continuation in part of co-pending, co-owned PCT International Patent Application PCT/US04/006409 filed Mar. 1, 2004, designating the United States of America, and published in English as WO 2004/078235, which is a continuation in part of U.S. Ser. No. 10/379,222, filed on Mar. 4, 2003, now U.S. Pat. No. 7,112,177, the contents of both of which are incorporated by this reference in their entirety.

FIELD OF THE INVENTION

The invention relates generally to plumbing devices including valves and conduits, and to pressure measurement equipment. The invention relates particularly to apparatus configured as an assembly to infer intra-abdominal pressure of a medical patient by measuring the pressure of fluid in the patient's bladder.

BACKGROUND

Elevated intra-abdominal pressure leads to major changes in the body's physiology that, if undetected and untreated, can result in organ damage and patient death. When patients become critically ill, they may develop a capillary leak phenomenon that causes the tissues in their body to become edematous with extra fluid that seeps out of the capillaries. This process is called "3rd spacing" of fluid. It is very common in sepsis, burn, trauma and post-operative patients. One area of the body where 3rd spacing is especially prevalent is the abdominal cavity. Critically ill patients can have many liters of fluid leak into the intestinal wall, the intestinal mesentery, and the abdominal cavity (as free fluid sloshing around the intestines).

Fluid 3rd spacing in the abdominal cavity results in an increase in intra-abdominal pressure (IAP). Normal IAP is 0 mm Hg to subatmospheric (less than 0). Once the pressure builds to 12-15 mm Hg, intra-abdominal hypertension (IAH) occurs. At this point, methods to improve intestinal perfusion should be started, such as: fluid loading to increase blood flow to gut, inotropic support to increase cardiac output, etc. As pressures increase above 20-25 mm Hg, the abdominal compartment syndrome (ACS) exists and major physiologic and organ system dysfunction result. Decompressive surgery (vertical midline abdominal incision) is often required to prevent irreversible organ damage and death. The exact pressure at which abdominal decompression should occur is dependent on a number of host factors including age, underlying co-morbidities and physiologic evidence of developing ACS.

Early detection of increasing abdominal pressure allows the clinician to intervene before irreversible organ damage occurs and may be life saving. The only reliable method for early detection of increasing IAP is to place a catheter within a space in the abdomen (peritoneal cavity, stomach, bladder, rectum) and measure the pressure. The most commonly used method is to monitor bladder pressure through an indwelling Foley catheter. To monitor bladder pressure, clinicians are currently building their own devices out of many separate materials and inserting them into the Foley catheter.

Currently employed techniques used to monitor a patient's IAP are adapted to measure the pressure of fluid contained within the patient's bladder at intervals spaced apart in time. While the pressure reading at a pressure transducer may not correspond to the actual value of IAP (e.g. if the transducer is located at a different elevation than the bladder), trends in measured pressure will correlate to trends in IAP in the patient.

One way to measure a patient's IAP involves disassembling a urinary catheter drain tube to inject saline through the catheter and into the patient's bladder. (For convenience, a urinary catheter will generally be referred to in this disclosure as a Foley catheter, due to its common use). Unfortunately, opening the closed drainage system plumbing places both the patient and the health practitioner at increased risk of infection. It is possible to use a three-way Foley catheter, but such catheters are more expensive and are not routinely used. Use of a three-way Foley catheter would require either preknowledge of its necessity, or replacement of a standard catheter. The former option increases costs, and the latter would increase both costs and risk of patient infection.

A different approach for introducing a bolus of fluid into a patient's bladder incorporates the aspiration port included in a urinary catheter drain system as a fluid injection port. The drain tube connected to the Foley catheter is blocked, and the needle of a syringe is passed through the drain tube's aspiration port to permit injection of a saline bolus. A manometer or pressure transducer is then connected to the needle to record bladder pressure. Undesirably, approaches involving use of needles, particularly in the vicinity of the patient's legs to assemble the pressure measuring apparatus, place both the patient and the health practitioner at risk of needle sticks.

With reference to FIG. 1, a currently used arrangement adapted to monitor a medical patient's IAP is generally indicated at 100. A patient is fitted with a urinary catheter 102, such as a Foley catheter. A fluid source, such as saline bag 104, is connected in fluid communication to the catheter 102 upstream of an occluding device 108 temporarily applied to block the catheter drain conduit 106. Interruption of the urine drain path from the patient generally is permitted only temporarily as required to effect pressure measurements.

The device 100 includes a pair of two-way or three-way stopcocks, 110 and 112, respectively. One end of fluid supply tube 114 is connected to a one liter saline bag 104. The other end of fluid supply tube 114 is connected to an inlet port of stopcock 110. A valve stem in stopcock 110 may be oriented to permit fluid to flow from bag 104 toward syringe 116. When syringe 116 is full, or charged with fluid as desired, the valve stem of stopcock 110 is adjusted by way of a manual rotation to permit fluid flow from the syringe toward stopcock 112 while resisting fluid flow toward bag 104. Stopcock 112 can be adjusted to direct a bolus of fluid from syringe 116 for flow through tubing 120 towards catheter 102. Stopcock 112 may also be adjusted to an alternate configuration to provide fluid communication between a pressure measuring device 121 and tubing section 120 while resisting fluid flow toward stopcock 110. An infusion needle or angiocatheter 122 carried at an end of tubing 120 is inserted into urine collection port 125 to couple the tube 120 in fluid communication to the catheter 102.

The steps typically required to measure a patient's IAP, using the arrangement of FIG. 1, are as follows: First the apparatus 100 is assembled, including inserting the needle of an angiocatheter 122 into aspiration port 125 connected to a Foley catheter 102 installed in a patient. Stopcock 110 is oriented to permit fluid flow between bag 104 and syringe 116, and the syringe is filled with saline. Stopcocks 110 and 112 are then both adjusted for fluid flow from the syringe 116 toward the catheter 102. Tube 120 is flushed and filled with saline. Then tubing 106 is occluded to resist fluid flow in a drain direction from catheter 102. Typically, stopcock 112 is then adjusted to resist fluid flow toward syringe 116 and stopcock 110 is configured to permit fluid flow between bag 104 and syringe 116 so that the syringe 116 can be refilled with saline. After priming syringe 116, stopcock 110 and 112 are adjusted for fluid flow between syringe 116 and catheter 102 to place a bolus of fluid into the patient's bladder. Then, stopcock 112 is oriented to provide fluid communication between conduit 120 and pressure transducer 121 while resisting fluid flow toward stopcock 110. Pressure apparatus 121 then indicates the current pressure in the patient's bladder, which may be correlated to IAP. Subsequent to making and recording the pressure measurement, the occlusion of drain 106 is removed to permit draining the bolus of fluid from the patient's bladder. Such procedure is repeated at intervals spaced apart in time to record trends in the patient's IAP. The bolus of injected fluid desirably is less than about 100 mL and of uniform size during each successive pressure measurement to avoid effect from bladder wall musculature on measured pressure.

Occluding device 108 may be a clamp or hemostat as illustrated, or sometimes may be a manually operated valve. However, operable medical grade valves that are commercially available, such as two-way or three-way stopcocks 110 and 112, typically introduce undesired complications. One complication is that the available medical grade stopcocks typically provide drainage passageways that are too small in diameter for use in a urinary catheter drain. Clogging of the urine drain bore would be a serious problem.

The most desirable location of a catheter drain-occluding valve (urine valve) for an IAP measurement system is in close proximity to the catheter 102—therefore between the patient's legs. Another complication substantially precluding direct inclusion of commercially available medical grade two-way or three-way valves or stopcocks is that such devices route fluid conduits in orthogonal directions at the valve connection locations, thereby creating protruding and invasive plumbing that is uncomfortable to the patient. Furthermore, currently available valves and stopcocks also have protrusions (such as valve actuators or handles), and sharp corners or abrupt changes in shape, that place a patient at risk of injury should such protrusion or corner be impressed into a patient's skin.

Because the most desirable plumbing arrangement places the urine valve between a patient's legs, manual actuation of that valve requires a health practitioner to gain physical access to the groin area of a patient. In a surgical setting, the anesthesiologist is the most likely party to assume responsibility for monitoring the patient's IAP. Traditionally, the anesthesiologist is stationed at the patient's head for convenient administration of anesthesia and monitoring of the patient's condition. All monitoring apparatus required by the anesthesiologist desirably is located in close proximity, or in a line-of-sight, to reduce moving about of personnel in the operatory theater.

Historically, in surgeries not involving the head of a patient, the patient's head area is regarded as the "turf" of the anesthesiologist. Correspondingly, the rest of the patient's body is regarded as the "turf" of the surgeon. It is undesirable for the anesthesiologist to move from a traditional station, at the patient's head, repeatedly to make periodic IAP measurements. Further, it would be impolitical to require an anesthesiologist to invade the "turf" of the surgeon to effect the IAP measurement. In any case, periodic manual activation of a urine valve by the anesthesiologist, or other personnel present in the operatory, also may cause an interference with the surgeon.

A variety of valves of various types may be employed in a system to measure IAP. One known plumbing device, typically used to remove a blockage from a drain, may be regarded as a valve, and has a sealing arrangement structured like a balloon disposed inside a pipe. The plumbing device is attached to a hose, and placed through an opening into the blocked drain pipe. Water forced under pressure through the hose inflates the plumbing device to seal the opening into the pipe. Additional water flow through the plumbing device's balloon pressurizes the pipe, hopefully, to flush the blockage downstream through the pipe. Importantly, a fluid path extends from the hose, through the balloon, and into the pipe. The wetted membrane of the aforementioned balloon-in-a-pipe forms a fluid excluding boundary, and creates a 2-dimensional seal interface at a circumference around the inside of the pipe. In correct operation of the plumbing device, fluid never flows between the wetted membrane of its balloon and the interior of the pipe.

A flow-regulating device known as a FLOWGRID valve is described on the world wide web at http://www.mooneycontrols.com/index-products.html. A representative such device is designated a 2" Large Single Port FLOWGRID valve. Such valves have a pneumatically actuated diaphragm valve element that is biased toward a valve-closed position to restrict fluid flow through the valve. The membrane element is adapted and arranged to occlude the area bounded by the circumference of an entrance orifice, thereby forming a 2-dimensional seal area.

The procedures for measuring trends in a patient's IAP described above undesirably place a patient at risk of infection, or require tiresome manual adjusting of a plurality of plumbing devices, such as two-way valves or stopcocks. It would be a desirable improvement to provide a device for measuring trends in a patient's IAP that is faster and more simple to operate. It would be a further advance to eliminate operations requiring needles to assemble or use the pressure measurement apparatus. A still further advance in the art would enhance the patient's comfort and increase the patient's protection from injury by resisting contact between the patient and uncomfortable or even harmful medical apparatus. A still further advance would provide for actuation of the urine drain valve from a location remote from that valve. It would be an improvement to provide such a valve that is low cost, enhances patient comfort, and/or provides an inherent time-delay in actuation between closed and draining positions. A still further improvement would provide a normally-open valve having a membrane seal arranged for hydraulically-transverse actuation.

BRIEF SUMMARY OF THE INVENTION

The instant invention provides an improved valve and a method of using that valve. One exemplary use of the invention is in an assembly disposed in fluid communication with the bladder of a medical patient to infer intra-abdominal pressure (IAP). Such LAP measurement procedure can be performed with a partially or fully automated system. Preferred embodiments of the invention incorporate manual fluid pumping with automated urine valve actuation effective to record IAP at programmed intervals of time without requiring further human intervention to ensure opening of a fluid path to permit draining of urine from the patient. Pressure measurements can be displayed at local and/or remote locations.

Therefore, a health practitioner can remain at a remote central location and monitor the vital statistics, including IAP, of a plurality of patients.

An operable urine valve may be embodied as a hydraulically actuated valve having a housing configured and arranged to permit fluid communication between an entrance port, a control port, and a drain port. One exemplary such valve includes a seal member arranged inside the housing for hydraulic actuation between a valve-open position and a valve-closed position. The exemplary valve also includes a fluid-flow restriction valve disposed in a first fluid path along which control fluid may flow from the control port toward the entrance port. Preferably, the fluid-flow restriction valve is structured to generate a back-pressure responsive to a flow of control fluid to urge flow of actuation fluid toward the seal member. Also, the exemplary valve generally includes a bleed-down port configured and arranged to permit evacuation over a time period, as bleed-down fluid, of actuation fluid confined by the seal member.

In a currently preferred embodiment of an automatic hydraulic valve, subsequent to being displaced beyond a valve-closed position, the seal member is biased to urge bleed-down fluid to flow through the bleed-down port effective to cause a time-delayed automatic opening of the valve. A workable seal member for such valve can be an expandable diaphragm configured and arranged to be self-biased from a valve-closed position toward a valve-open position. One way to generate a time-delay prior to automatic valve opening incorporates a bleed-down valve arranged in-circuit to slowly discharge a timing volume created by displacement of the seal member. Such timing volume can be created by inflating the membrane beyond a valve first-closed position to encompass a confined volume in excess of that volume required to form an initial blockage of draining fluid flow in a drain path through the valve.

One preferred embodiment of a hydraulically actuated valve may be characterized by providing a plurality of fluid paths. In such valve, a first path may be defined between an entrance port and a drain port. A portion of the first fluid path may be provided by structure associated with the valve's housing and disposed between a control port and the entrance port. A second fluid path can be defined between the control port and the drain port. A bleed-down port of the valve is arranged to discharge bleed-down fluid along a path that overlaps a portion of that second fluid path. Bleed-down fluid can be directed along a third fluid path between the bleed-down port and a fluid-flow restriction valve. Desirably, a bleed-down valve is associated with the bleed-down port to cause the rate of flow of bleed-down fluid to be sufficiently low that it does not generate a significant back-pressure when passing through the flow-restriction valve. At certain times during valve operation, a fluid path followed by the bleed-down fluid overlaps a portion of the first fluid path.

A preferred embodiment of a hydraulically actuated valve may be characterized by structure associated with a blockage of a drain path through the valve. Such valve includes a seal member having a membrane arranged to form a traveling wall operable to collapse a cross-section of a draining lumen effective, in cooperation with valve-closing seal structure carried by a fixed wall, to form a blockage structured to resist draining fluid flow through the valve. A sealing perimeter can be defined as a wetted boundary formed by contact of the membrane onto cooperating fixed seal structure when the membrane is displaced to a valve first-closed configuration. Sometimes, the sealing perimeter is noncircular. In certain embodiments, the sealing perimeter is a 3-dimensional entity. Structure forming a seal to resist draining fluid flow may be configured and arranged such that a normal to a portion of a bounded seal area has a component oriented substantially perpendicular to a vector indicating valve-open fluid flow through the lumen opening defined by the perimeter of the bounded seal surface.

The instant invention may be embodied as a normally-open, hydraulically actuated, automatically opening valve. Structure generally associated with body of such valve include a control port, an entrance port, and a drain port. In general, the valve is operable to resist draining fluid flow along a normally-open first flow path between the entrance port and the drain port. The valve body defines an expansion chamber disposed in fluid communication between the entrance port and drain port. Typically, the expansion chamber includes one or more timing chambers arranged in association with the membrane to accommodate over-inflation of the membrane, by timing fluid, beyond a first valve-closed position. Desirably, the expansion chamber carries valve-closing seal structure on a fixed wall. A membrane is arranged to receive fluid communication from the control port effective to cause a traveling wall to collapse a cross-section through the first flow path in the expansion chamber and create, in cooperation with the valve-closing seal structure, a blockage of the first flow path. Desirably, the membrane is biased from a valve-closed position toward a valve-open position. Therefore, a bleed-down port configured and arranged to permit discharge of timing fluid confined by the seal member can cause a time-delay prior to removal of the blockage, and opening of the first fluid path for draining.

The instant invention provides a method, for hydraulically actuating a valve, to block a drain path through the valve. Such method includes the steps of: providing control fluid to the valve by placing a fluid source in fluid communication, through a pressure-inducing apparatus, with a control port of the valve; operating the pressure-inducing apparatus to urge a flow of control fluid through the control port toward a fluid restriction port operably to generate a back-pressure in control fluid, thereby causing actuation fluid to displace a diaphragm from a normally-open position to a first-closed position effective to occlude the drain path; further operating the pressure-inducing apparatus to urge a flow of timing fluid, thereby causing additional displacement of the diaphragm effective to create a timing volume; stopping operation of the pressure-inducing apparatus; and waiting during a time-delay while the timing volume is permitted to drain through a bleed-down port to permit the diaphragm to return to a valve-open position.

A method according to the instant invention may be practiced when the valve is included in an assembly adapted to periodically measure the bladder pressure in a medical patient to infer the abdominal pressure in that patient. In such case, the method may also include the steps of: installing a urinary catheter in the patient to provide fluid communication between the bladder and a discharge portion of the catheter; disposing an entrance port of the valve in fluid communication with the catheter so that the valve can provide a drain orientation and a measure orientation, with the drain orientation permitting fluid flow from the entrance port through the valve and along the drain path toward a receptacle, and with the measure orientation providing fluid communication between the entrance port and the control port while the drain path is occluded; disposing a pressure transducer in-circuit effective to measure the pressure of fluid in the bladder; operating the pressure-inducing apparatus to place the valve into the measure orientation and to introduce a bolus of control fluid into the bladder; and using the pressure transducer to measure a hydrostatic pressure of the fluid in the bladder during the time-delay.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

Figure 2:
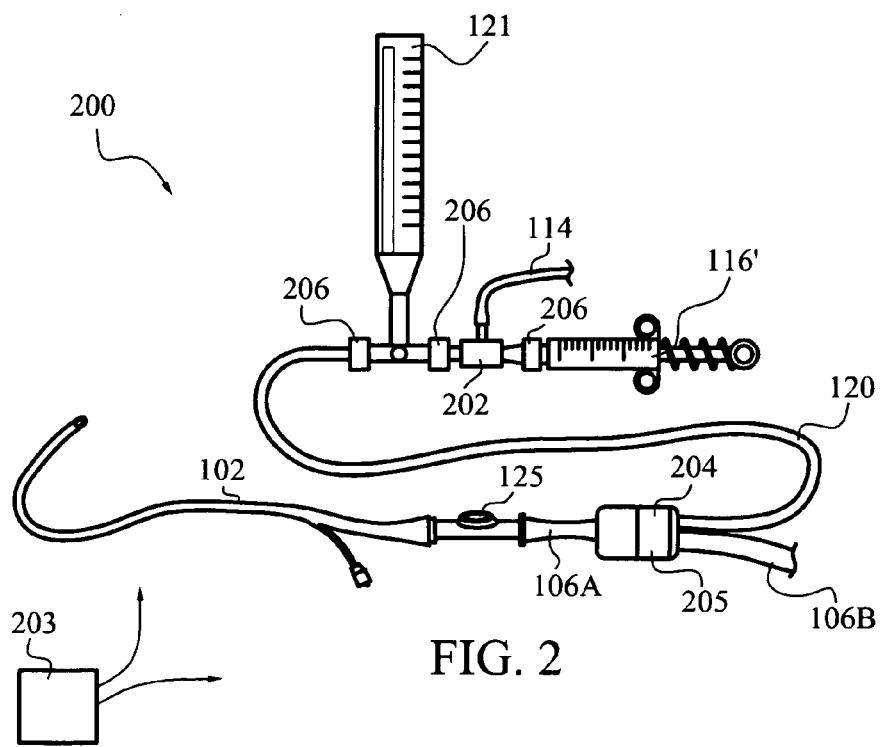
FIG. 2 is a schematic plan view illustrating a first assembly for measuring a patient's bladder pressure according to principles of the invention.

FIG. 2 illustrates an exemplary embodiment, generally indicated at 200, of an apparatus for measuring trends in a patient's intra-abdominal pressure. The assembly 200 includes a fluid supply conduit 114 with one end in fluid communication with a sterile saline or other fluid source (not illustrated). Conduit 114 desirably is connected at a second end for fluid communication with an automatic, direction-of-flow control device 202 to urge fluid flow through conduit 120 in a direction toward a patient. A hydraulic pressure in conduit 120 is measured by a pressure transducer, such as transducer 121.

Figure 1:
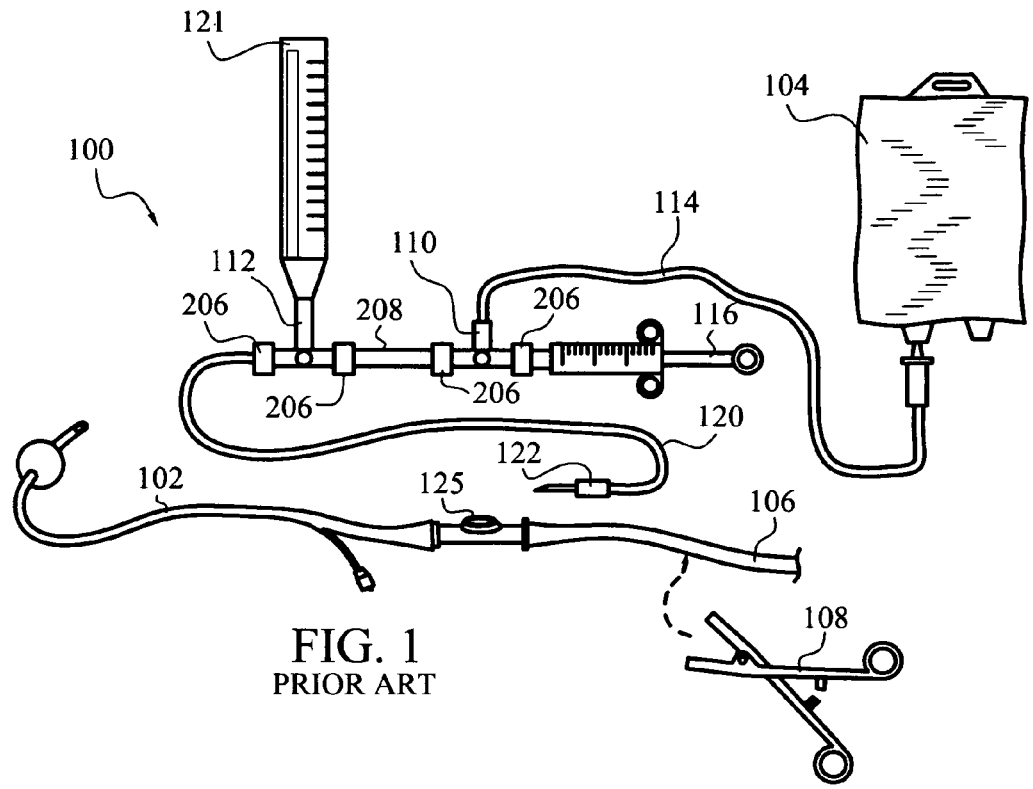
FIG. 1 is a schematic plan view illustrating a prior art assembly operable to measure a patient's bladder pressure.
Figure 3:
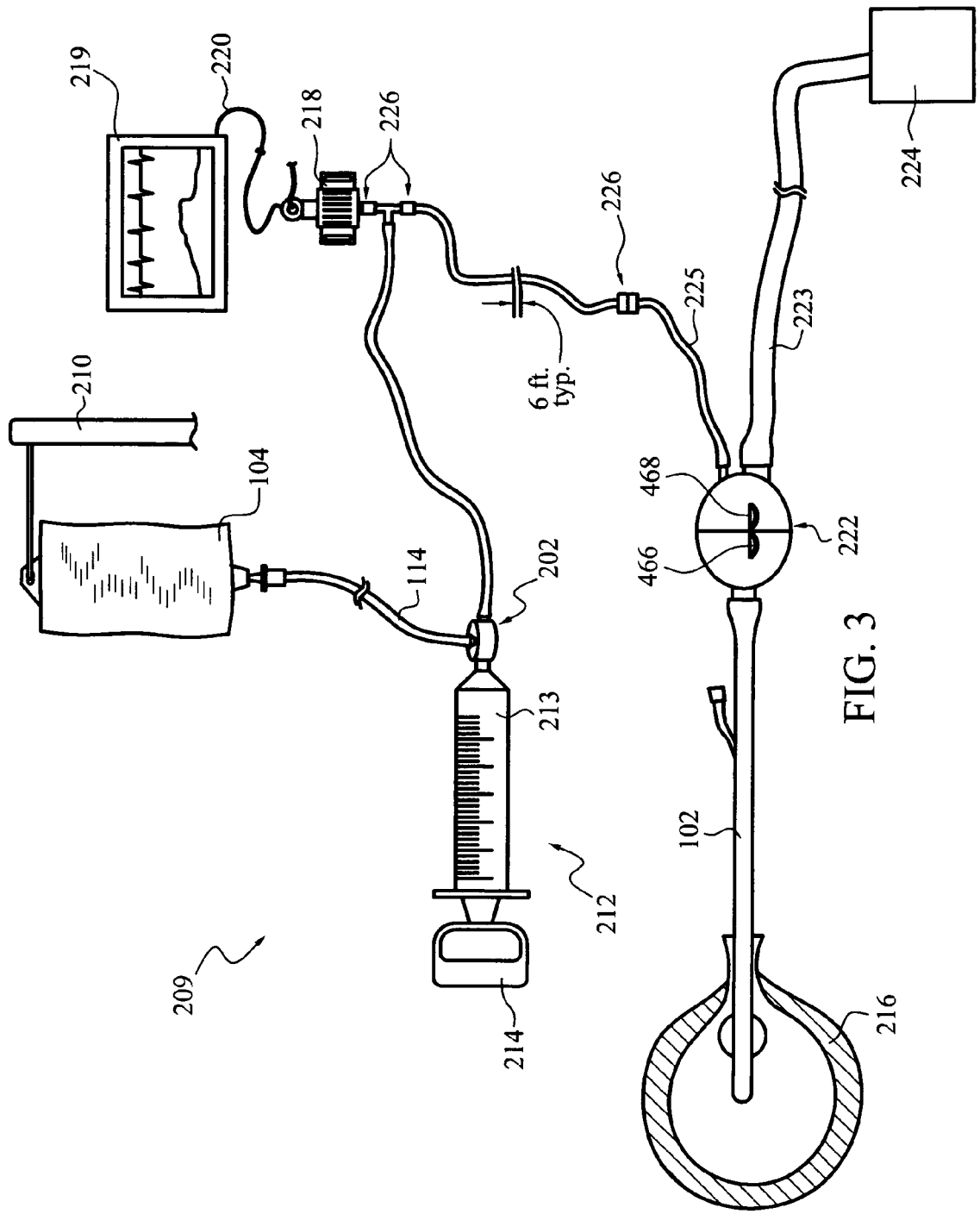
FIG. 3 is a schematic plan view illustrating a second arrangement of equipment for measuring a patient's bladder pressure according to principles of the invention, which locates a pressure transducer remote from the patient.

As illustrated in FIG. 3, it is sometimes preferred to arrange the pressure transducer in a dead-ended conduit, compared to the flow-through arrangements illustrated in FIGS. 1 and 2. The illustrated arrangement requires a clinician to make only one attachment at the pressure transducer area. However, it should be realized that additional components, such as zeroing stopcocks, may be included in desirable alternative plumbing arrangements and may not be illustrated in certain of the FIGs. for various reasons. For example, and with reference still to FIG. 3, such a zeroing stopcock often is placed into position at a joint 226 between the 'T' connector and the pressure transducer 218. Such a stopcock may be installed for convenience in purging air from the system, to facilitate maintaining a sterile field inside conduit 225, and/or to isolate the pressure transducer from the conduit system for purpose of establishing a baseline pressure, or zero, for an output of the transducer 218.

Desirably, a large portion of an IAP measuring apparatus is provided in a preassembled form, e.g. as a kit, to reduce decision making required of clinicians. With reference again to FIG. 2, one preferred embodiment of the invention is provided as a substantially preassembled kit-in-a-package 203. A preferred embodiment of the kit 203 reduces chance of error by simplifying assembly of an IAP apparatus and reducing the number of decisions a clinician must make. Certain of such kits requires a clinician only to make a first hydraulic connection to a saline bag 104, a second hydraulic connection to a pressure transducer, and a third hydraulic connection between an indwelling catheter and a urine drain container. Package 203 desirably is made from a material operable to maintain sterility of the components included in the kit as the kit is transported and stored prior to use.

Flow control device 202 can generally be characterized as being cyclically operable with a staging infusion pump, such as a syringe, to permit fluid flow from a fluid source during a filling stroke of the staging pump, and to resist fluid flow towards the fluid source during an expelling stroke of the staging pump. Typically, one or more seal members carried inside of device 202 is/are biased for automatic operation to control a direction of fluid flow through the device 202. Therefore, a health practitioner is relieved of the tedious chore of adjusting the valve 202 manually to control a direction of fluid flow between cycles of an infusion pump such as a syringe. Devices within contemplation for use as a flow control device 202 nonexclusively include a pair or more of check valves, a double check valve, a check-bypass valve, and a check/restricted flow-bypass valve. An operable flow control device 202 may sometimes be embodied by a single multifunction component, or may include an assembly of single- and/or multifunction devices.

As illustrated in FIG. 2, assembly 200 includes a remotely actuatable valve 204 connected in fluid communication with a discharge port from flow control device 202. Valve 204 may sometimes also be referred to in this disclosure as a type of urine valve, or a urine discharge or drain valve. Valve 204 desirably is located in close proximity to a discharge of a Foley catheter 102 installed in a patient. A Foley catheter is not required, per se.—virtually any sort of urine draining catheter may be used. One exemplary operable catheter is commercially available from CR Bard, Inc. of New Jersey, under part No. 265716.

As illustrated in FIG. 2, valve 204 can be connected in fluid communication to Foley catheter 102 by way of a relatively short section of urine drain conduit 106A. Such close proximity to a discharge of catheter 102 reduces a volume of fluid required to be pumped through the system to effect a pressure measurement, and also helps to maintain the apparatus 200 in a tidy, organized arrangement. Inclusion of a remotely actuatable valve, such as valve 204, to selectively block a discharge from the catheter 102 simplifies operation of the assembly 200 compared to the prior art, and constitutes an improvement providing several advantages.

Of course, a urine valve, such as illustrated valve 204, may be adapted to connect directly to the discharge end of a urinary catheter without an intervening conduit section 106A. It is within contemplation for a valve 204 to carry structure adapted for connection directly to structure provided at a discharge area of a catheter 102. In general, connections between the various components forming an IAP assembly, such as illustrated assembly 200, may be made as a matter of convenience, and using any operable type of plumbing connection joint.

In the embodiment illustrated in FIG. 2, valve 202 is connected to a discharge end of spring-assisted syringe 116' through a luer-locking type of joint 206. Such luer-locking joints are commonly used in medical plumbing arrangements. However, an alternatively structured connection between any of the components in an IAP measuring assembly within the ambit of the invention, such as assembly 200, may include any operable fluid-tight connection that is formable between the components.

Stretches between components may also include intermediate structure, such as one or more sections of tubing 208 (see FIG. 1). Furthermore, an embodiment of the invention, such as generally illustrated in FIG. 2 as assembly 200, desirably is configured for arrangement of its various components in convenient and/or desirable locations. For example, bag 104 typically is suspended from an elevated hanger, but pressure indicating manometer 121, or in alternative embodiments, a pressure measuring transducer, desirably is located at approximately the same elevation as the patient's bladder to reflect an equivalent pressure. Intermediate tubing members (e.g. 114, 120, 208. etc.) may be provided having lengths sized to permit a desired spacing between components.

With reference still to FIG. 2, preferred embodiments of a remotely actuatable valve 204 provide connections for fluid supply conduit 120 and urine drain conduit 106B to place such conduits approximately in parallel. A substantially parallel arrangement of conduits 120 and 106B near the valve 204 can increase patient comfort and also help to maintain a tidy arrangement of assembly 200. Furthermore, the illustrated substantially in-line arrangement between conduits 106A and conduits 120 and 106B aides in routing the conduits along a path effective to minimize their intrusiveness to a patient.

Fluid-carrying conduits may be affixed or connected to structure associated with one or more components when assembling an apparatus 200. It is currently preferred to include a short length, or pigtail, of infusion fluid supply conduit 120 permanently affixed to valve 204 when manufacturing the valve. Fluid supply conduits typically are of relatively small diameter (e.g. about 1/16 to 1/8 inches, or 1-1/2 to 3 mm, in inside diameter) to minimize priming volume. Such a pigtail conduit typically is solvent welded, or otherwise bonded to structure associated with valve 204. However, other connection arrangements are workable, including bayonet-style slip-on fits between a conduit end and a receiving nipple or barb.

The urine drain lumen downstream of the catheter, and passing through the urine valve, desirably is of relatively larger diameter (e.g. about 3/16 to 1/2 inch, or 4.8 to 13 mm, in inside diameter) to resist occlusion during extended periods of use. A discharge end of a catheter 102, or tube section 106A (see FIG. 2), may be stretch-fit, to make a connection in the field, over an exterior surface of a barb-type fitting associated with valve 204. In some cases, an additional external clamp may further be applied over the catheter 102 or conduit 106A to augment the formed joint, and to resist decoupling the patient connection from the valve 204 as a bolus of fluid is injected into a patient's bladder. Similarly, a discharge conduit 106B may be attached to urine valve 204 in a plug-together fit.

Certain preferred embodiments of a urine control valve 204 may include a valve body or housing 205 shaped to provide a comfortable interface for adjacent surfaces of a patient's skin to resist contact-induced patient discomfort. One such comfort-enhancing shape includes blunt edges and rounded corners. Certain valve actuation structure of a comfort-designed urine valve 204 desirably is disposed internal to valve housing 205 to avoid protruding elements that might poke and irritate a patient.

FIG. 3 illustrates an arrangement of equipment, generally indicated at 209, for measuring IAP in a patient that locates most of the equipment at a convenient location remote from the patient. While equipment can be located at any convenient distance from the patient, it is generally located within a radius of about six to ten feet, or so. In a surgery setting, apparatus to control making and observing an IAP measurement desirably is positioned for convenient access to an anesthesiologist. The IAP measurement equipment desirably is assembled using a procedure operable to resist degrading sterility of the catheter draining system.

As indicated in FIG. 3, apparatus including the saline fluid source 104 can be suspended from equipment stands, such as stand 210. Fluid flow control device 202 and a cyclic pressure-inducing device, such as syringe 212, may be located in convenient proximity to the saline bag 104, or at some other desirable location. Illustrated syringe 212 is representative of a larger model, perhaps having a volume capacity of 50 ccs. Such a syringe 212 typically is operated using both hands. An operator grasps the syringe barrel 213 with one hand and actuates the plunger held in the other hand at transverse handle 214. In preferred embodiments of the invention, cyclic actuation of the syringe 212 automatically operates the fluid flow control device 202 to urge fluid flow in the direction toward the patient's bladder 216.

It is desirable for a patient's bladder pressure to be accurately measured, and for that pressure value to be displayed and recorded. As one way to ensure such accuracy, pressure transducer 218 may be suspended from some convenient structure at an elevation substantially in correspondence with the patient's bladder. In an alternative arrangement, a "measured" pressure offset from true bladder pressure must be zeroed, or otherwise removed from data provided by the transducer 218. Two operable pressure transducers 218, commercially known as Truwave disposable pressure transducers, are commercially available from Edwards Lifesciences under part numbers PX601 and PX600F. Transducer 218 can be affixed to a wall, stand 210, a side of the patient's bed, the patient's leg, or any other convenient location. Pressure display terminal 219 can be located as desired for convenient monitoring by a health practitioner. An electric cable 220, or wireless transmission (not illustrated) communicates the pressure signal from the transducer 218 to the display device 219.

The urine discharge valve illustrated in FIG. 3, and generally indicated at 222, may be adapted for hydraulic actuation, from a location remote from the valve 222, between a draining and a blocking configuration. Such a hydraulic valve 222 is normally disposed in a draining configuration to permit discharge of urine, or other fluid, through urine catheter 102 placed into fluid communication with the patient's bladder 216. Valve 222 is normally placed into such drain configuration so that fluid drains from bladder 216, through valve 222, through drain conduit 223, and into urine collection facilities, such as bag 224.

Some urine valves 222 may include one or more sections of conduit, such as drain conduit 223 and/or fluid supply conduit 225 permanently affixed by known manufacturing methods to structure associated with the body of the valve 222. In such case, a connector, such as the luer-locking type connector generally indicated at 226, may be provided to facilitate making plumbing connections in the intra-abdominal pressure monitoring apparatus assembly.

Figure 4:
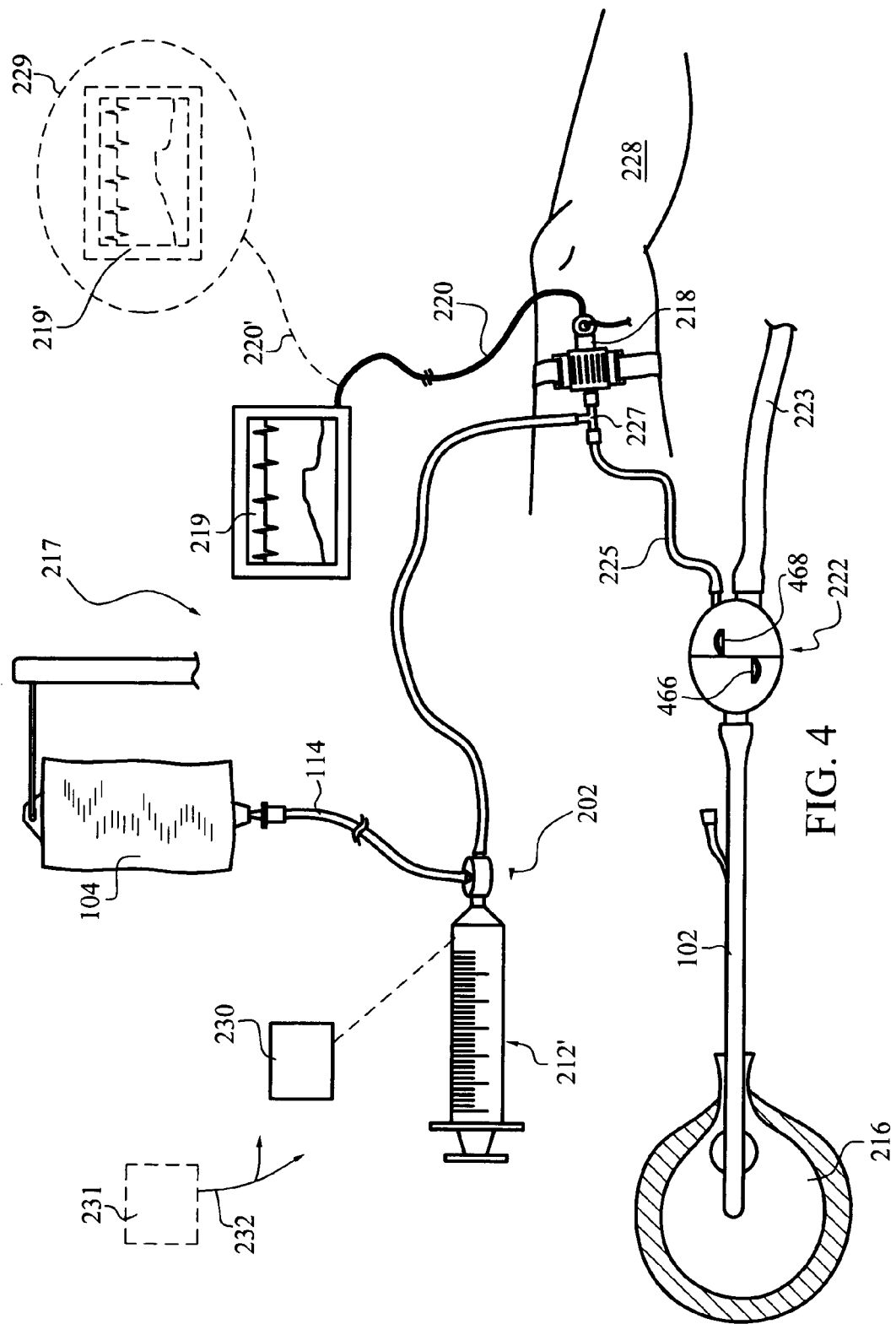
FIG. 4 is a schematic plan view illustrating a third arrangement of equipment for measuring a patient's bladder pressure according to principles of the invention, which locates a pressure transducer on the patient's leg.

The assembly to measure trends in IAP illustrated in FIG. 4, generally indicated at 217, locates the pressure transducer 218 on the patient's leg 228. A cyclic pressure-inducing device, such as the finger-actuated syringe generally indicated at 212', is illustrated in combination with a flow control device 202 for use of the thus-formed assembly as a fluid infusion pump.

Illustrated valve 222 may also be characterized as providing a streamlined plumbing arrangement, in that conduits 225 and 223 can be maintained in approximately parallel alignment in the vicinity of the valve 222. In contrast to an orthogonal plumbing arrangement provided by certain prior art valves, such a streamlined plumbing configuration facilitates routing of the conduits to reduce irritation to a patient. The streamlined plumbing arrangement provided by valve 222 urges conduits 225 and 223 to follow a path between the patient's legs where the conduits are most out-of-the-way, and less likely to impact negatively on patient comfort.

In the context of the instant invention, a terminal 219 encompasses any display device operable to show a representation of data for visual acquisition by a human observer. Representative terminals 219 include CRT's, LCD panels, LED arrangements, columns of mercury or other indicating fluids, and other devices capable of producing a visible display of a representation of data, such as numbers, line plots, or bar graphs, and the like.

More than one terminal 219 may be provided, with one typically being located near the patient's bed. In a surgical theater, one such terminal desirably is placed in a line-of-sight to the anesthesiologist. As illustrated in FIG. 4, one or more terminals 219' may be disposed at one or more locations 229 remote from the patient, such as at a central station adapted to monitor a plurality of patients, for remote monitoring of the patient by one or more health practitioners. Communication from the pressure transducer 218 to terminal 219' can be effected by wireless transmissions or through cable 220'.

Sometimes, when a urine valve, such as valve 222 in the plumbing arrangement illustrated in FIG. 4, is actuated from a pressure-measurement orientation to a drain orientation, a residual pressure remains in conduit 225 and undesirably is displayed on terminal 219. Therefore, sometimes a zeroing stopcock (not illustrated) may be included in the pressurized fluid path, e.g. such as in a location between three-way fitting 227 and pressure transducer 218.

In the assembly 217 illustrated in FIG. 4, the valve 222 can be a remote-actuated valve operated by hydraulic pressure generated by an infusion pump. The infusion pump generates pressure that is used to move a valve member in valve 222 from a drain position, in which the contents of the patient's bladder drain, to a blocking position, in which saline, or other fluid, can be infused into the patient's bladder.

Of course, alternative remote actuation mechanisms are within contemplation in the instant invention, nonexclusively including electrically actuated valves. In one electrically actuated valve within consideration, operation of the infusion pump may be slaved to an electromechanical urine valve.

In general, urine valves operable in the present invention may be actuated by human action, hydraulically, or electromechanically. Infusion pumps may similarly be actuated. The entire IAP procedure lends itself to automation to remove a tedious, error prone, burden from health practitioners. With reference to FIG. 4, the pumping system including syringe 212' can be replaced by an automated infusion pump 230. The infusion pump 230 and urine valve 222 can be placed under the control of a control device 231, which can be programmable. Control device 231 can be arranged to communicate with pump 230 (and automated valve 222 in certain cases), using wireless transmissions or wires 232. The collected IAP data is then displayed at convenient locations, such as one or more of terminals 219 and 219'.

The plumbing arrangement illustrated in FIG. 4 can undesirably indicate a "false" pressure, e.g. during the interval when a hydraulically operated remote-actuated valve 222 is actuated between a draining configuration and a bladder infusion or IAP measurement configuration. At such time, the pressure required to actuate the valve 222 is displayed on terminal(s) 219, 219', which does not truly reflect the IAP of the patient. To reduce potential for confusion, it sometimes is preferred to arrange the transducer 218 in a plumbing arrangement more conducive to indicate only the pressure in the patient's bladder. One such arrangement is illustrated in FIG. 5.

Figure 5:
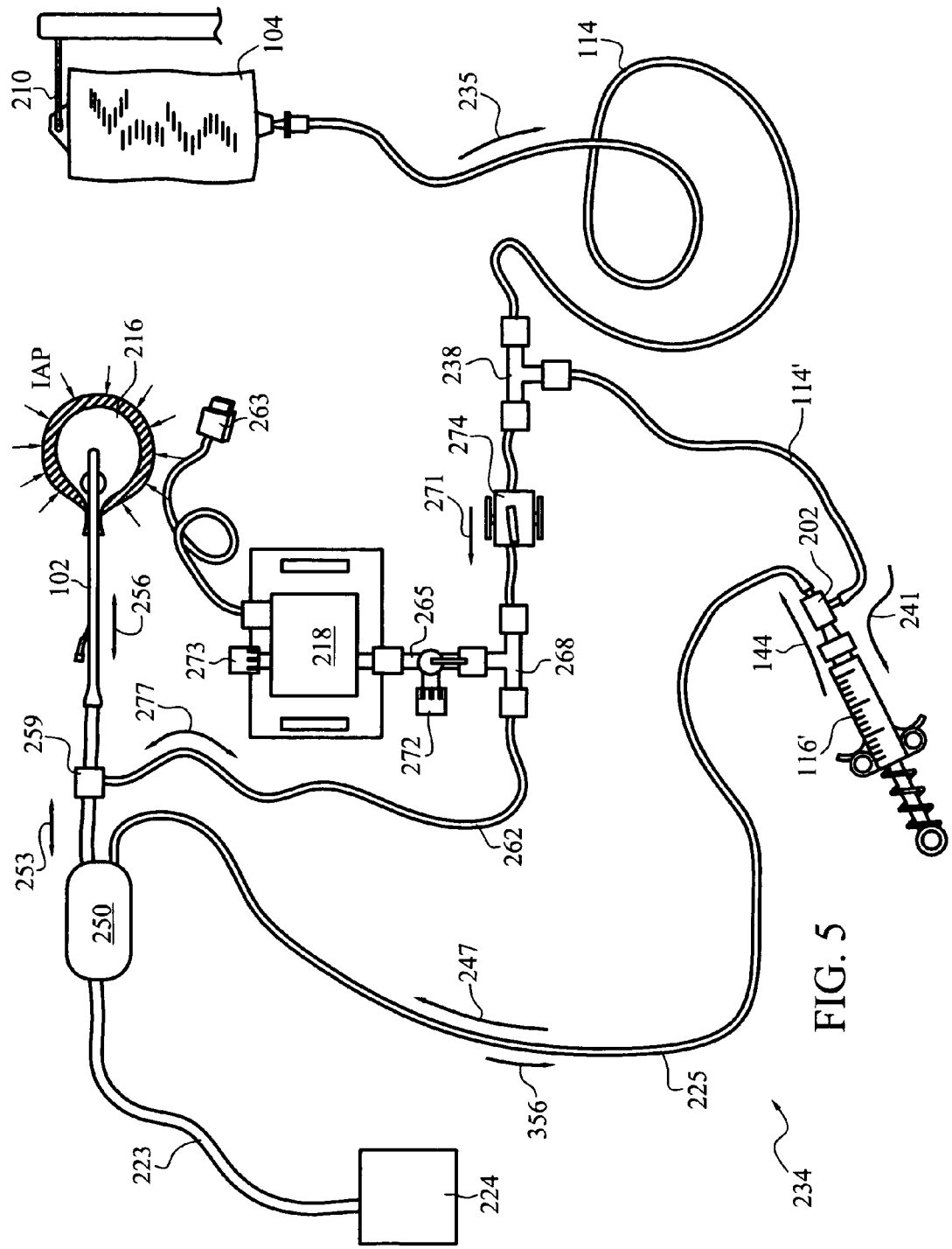
FIG. 5 is a schematic plan view illustrating a fourth arrangement of equipment for measuring a patient's bladder pressure according to principles of the invention.

FIG. 5 illustrates one currently preferred plumbing arrangement, generally indicated at 234, operable to connect devices effective to measure the LAP of a patient in substantial isolation from pressure spikes associated with operation of fluid transfer devices. The fluid source may be a saline container 104, as illustrated. In certain arrangements, the saline bag 104 desirably is disposed at an elevation on stand 210, and/or placed into a pressurizable container to generate a "head" pressure in the bag 104. One operable air-activated pressurizable container, generally known as a pressure infuser, is commercially available from the David Clark Company of Worcester, Mass., under the part number 18565G-02, uses an applied air pressure to cause a head pressure in a saline bag 104.

Fluid supply tubing 114 transports saline from the bag 104 under action of a cyclic pump, such as by way of operation of syringe 116'. As illustrated, supply tubing 114 forms a fluid path, indicated by arrow 235, between the bag 104 and a 'T'-fitting 238. Fluid supply tubing 114' continues a fluid path, indicated by arrow 241 toward a flow control device 202. Fluid transported along flow path 241 loads into the syringe as the plunger is retracted. When the syringe's plunger is depressed, loaded fluid flows through fluid supply tubing 225, as indicated by arrows 244 and 247, and into the urine valve 250. A urine valve 250 may be actuated between draining and occluding configurations by direct manual manipulation of valve structure, or by remote actuation.

In certain embodiments of the invention, it is preferred to use some sort of hydraulically actuated valve as a urine valve 250 to provide a capability for remote actuation of the valve. In such case, energy imparted by the cyclic pump is used to actuate such valve from a draining configuration to an infusion configuration. A plurality of flow control devices are operable as fluid control device 202, as will be discussed further below, depending upon hydraulic requirements of the particular valves 250 employed in the fluid circuit. Similarly, various types of syringes are operable as cyclic pump elements. A choice for a particular type of syringe, e.g. spring-assisted such as syringe 116', or hand-operated such as syringe 212, may also be determined by hydraulic requirements of the valve 250 or of other components in the assembly.

In general, once a hydraulic valve 250 is actuated from a draining to an infusion configuration, an additional flow of fluid along path 247 will continue along the flow path indicated by arrows 253 and 256, and into the patient's bladder 216. Once a sufficient bolus of fluid is infused into bladder 216, operation of the fluid pump is stopped, and the pressure of the fluid in the patient's bladder may be measured to infer his/her IAP.

The plumbing arrangement illustrated in FIG. 5 is configured in an effort to indicate the true bladder pressure in the patient at all times. Desirably, a connection 259, effective to place pressure conduit 262 into fluid communication with fluid in path 256, is disposed in-circuit between the bladder 216 and the obstruction in path 253 provided by valve 250. In such an arrangement, pressure generated by the pump and required to actuate the valve 250 is not communicated to pressure transducer 218. Illustrated pressure transducer 218 includes a plug 263 for connection to a monitor, terminal, or other data collection device(s) for display and/or recording of pressure readings.

While connection structure 259 is illustrated in FIG. 5 as being a separate component, such structure 259 may be associated with (or part of) a valve 250. Furthermore, connector 259 may be configured to assist in maintaining a streamlined, more parallel, arrangement of fluid conduits in the patient's groin area. Similarly, fluid supply tube may be associated with a valve 250 to assist in parallel routing of conduits. For example, fluid supply conduit 225 may be connected to structure at the distal end of valve 250, rather than as illustrated being connected to the proximal end. It is within contemplation for connection structure 259 to encompass alternative conduit structure including a luer-activated connection at a sampling port of a conduit structured for engagement at a discharge end of the catheter 102. One such alternative conduit structure is commercially available as a component of a urinary drainage bag system available from Bard Medical, a subsidiary of CR Bard, Inc., under the part number 154002.

In the preferred arrangement 234 illustrated in FIG. 5, pressure transducer 218 is in fluid communication with pressure conduit 262 through stopcock 265 and 'T'-fitting 268. It should be realized that the presence of stopcock 265 and 'T'-fitting 268 is not essential. Pressure conduit 262 could be connected to stopcock 265 or directly to pressure transduce 218. In an alternative operable configuration, the positions of transducer 218 and stopcock 265 could be reversed. However, stopcock 265 and 'T'-fitting 268 promote ease of assembly and priming or flushing, and provide additional hydraulic control options. 'T'-fitting 268 allows fluid to flow along the path indicated by arrow 271 from 'T'-fitting 238. Such fluid flow along path 271 can be used conveniently to flush air and bubbles from a fluid flow path including the pressure conduit 262 and pressure transducer 218. Cover caps 272, 273 can be closed subsequent to purging air from the system.

Preferably, a fluid-flow restriction device 274 is disposed in path 271. Flow restriction device 274 is effective to isolate pressure transducer 218 from any head pressure (psig) associated with the fluid source 104. An operable flow restriction device includes an available valve commercially known as a Delta-Flow, which can be obtained from Utah Medical under part No. 100-204 at internet address http://www.utahmed.com. Such device has a minimum normal flow rate of about 3 ml/hr. At the low flow rate normally permitted by device 274, any fluid flowing along path 271 will be accommodated by expansion of the bladder 216, and therefore will not impact on a pressure indicated by transducer 218.

Typically, the diameter of the catheter 102 is larger than the diameter of conduit 262. A human bladder 216 can change its size rapidly to accommodate a significant volume change under a relatively low applied pressure. Desirably, conduit 262 is placed into fluid communication with flow path 256 in close proximity to the bladder 216. Therefore, catheter 102 and bladder 216 form a system providing a lower impedance to fluid flow than conduit 262. A flow of drip-infused fluid is accommodated by expansion of the bladder substantially to isolate pressure transducer 218 from such drip-infusion fluid flow. However, fluid flow through a primed conduit 262, responsive to pressure changes in the bladder, is substantially insignificant, so pressure changes in the bladder are indicated by pressure transducer 218 in substantially real time.

Desirably, device 274 can be actuated from its normal slow-flow configuration to permit a more rapid fluid flow along path 271 to facilitate flushing air from the downstream conduits and components. Illustrated device 274 can be squeezed to actuate it and change its flow characteristics to permit a more rapid, flushing fluid flow. Once the pressure transducer 218 and pressure conduit 262 are flushed, a column of fluid remains, providing 2-way communication, along a path indicated by arrow 277, with fluid in flow path 256. A low flow rate (drip-infusion) in a direction through conduit 262 toward connector 259 is desirable to resist migration of urine or contaminated fluids along path 277 toward pressure transducer 218 during extended periods of use of an LAP assembly.

Figure 6:
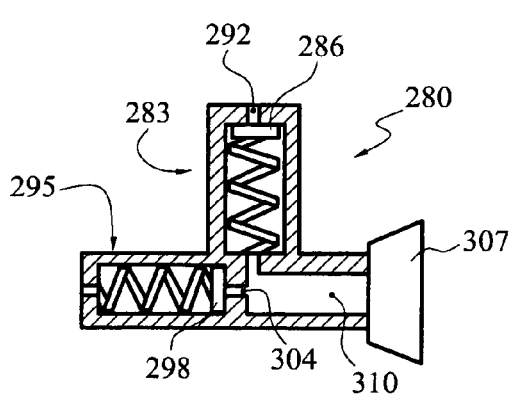
FIG. 6 is a side view, partially in section, illustrating a double check valve.

FIGS. 6 through 9 illustrate three types of valves that are operable for use as an automatic flow-control device 202 (see FIGS. 2-5). FIG. 6 illustrates a double check valve, generally indicated at 280. One check valve portion, generally indicated at 283, is formed by a sealing element 286 normally biased into engagement with an inlet opening or port 292. A second check valve portion, generally indicated at 295, is formed by sealing element 298 normally biased into engagement with exit port or opening 304. A pressure-cycling pump device, such as a syringe, may be connected in fluid communication with exit port 304 at a third port or conduit through connector 307. The syringe cyclically effects the fluid pressure at a staging area 310 and thereby automatically operates the check valve portions 283 and 295 in correspondence with the high or low pressure generated by the syringe.

Of course, a fluid circuit assembly equivalent to a fluid flow-control device, such as double check valve 280, can be formed by a pair of single check valves and a syringe 116 (or other cyclic-pressure pump) disposed between the two individual check valves. In certain embodiments, a single check valve may be included in a pressure measuring apparatus 200. In one such embodiment, the discrete check valve is located in the fluid path between a fluid source and a syringe 116 to enable multiple syringe discharges without requiring manual valve adjustments to reload the syringe with fluid.

Figure 7:
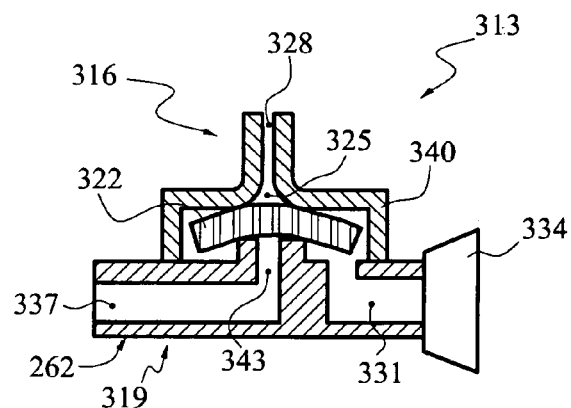
FIG. 7 is a side view, partially in section, illustrating a check-bypass valve operable as a double check valve in the invention.
Figure 8:
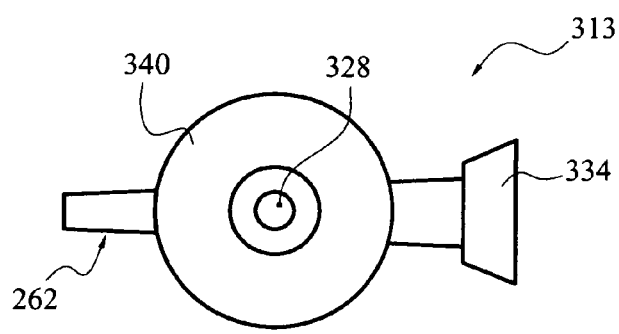
FIG. 8 is a top view of the valve of FIG. 7.

FIGS. 7 and 8 illustrate an embodiment of a check-bypass valve, generally indicated at 313, configured for use in the instant invention. Valve 313 includes a check valve portion, generally indicated at 316, and a bypass valve portion, generally indicated at 319. Check valve portion 316 is formed by resilient member 322 biased into normally sealed engagement over orifice 325. In operation of check valve 316, fluid flows into supply port 328, and past resilient member 322, to a staging area 331. In accordance with one definition of a check valve, fluid flow in the reverse direction would cause seal member 322 to seal tighter over orifice 325, thereby further resisting the flow.

Typically, staging area 331 is in fluid communication with a syringe, such as syringe 116' illustrated in FIG. 2. A cyclic pump may alternatively be employed to vary the pressure in the staging area 331 to operate the valve 313. A syringe may be attached directly to connection structure 334, or may be spaced apart from the valve 313 by use of structure such as a length of tubing.

It is currently preferred for connection structure 334, 307 to be structured as a LUER-LOK™ type fitting, and for structure surrounding inlet port 328 and discharge port 337 to accommodate attachment of tubing by way of a press-on fit. However connection structure 334 may be structured as any other operable connecting structure, including barbs configured for press-fit reception in, or over, a conduit. Likewise, any portion of a valve 313 (or a valve 280, or any other component), that is adapted for connection to a fluid conduit or other device may be structured to form a press-together fit, or to incorporate a portion of a LUER-LOK™ type joint, or a threaded connection, or as any joint providing fluid through-flow and structured to resist fluid leaks.

The illustrated bypass valve portion 319 can operate substantially as a check valve. However, under certain conditions, fluid can flow in either direction between port 337 and staging area 331. In use with the instant invention, pressurized fluid in the staging are 331 causes resilient seal member 322 to deflect into the orifice 325 of housing 340, thereby opening a flow path from staging area 331 though exit port 343 and out of discharge port 337. Contrary to a true check valve, increased fluid pressure at exit port 343 tends to open the flow path by lifting seal member 322 from engagement over exit port 343. Therefore, in certain situations, fluid could flow from discharge port 337 and into staging area 331. In that event, the fluid presumably could be refilling a syringe.

Bypass valve portion 319 is normally closed. Resilient member 322 is biased into sealing engagement over exit port 343 during assembly of the valve 313. Therefore, valve 319 operates as a check valve, to permit fluid flow in only one direction, until fluid pressure at exit port 343 builds to a value operable to overcome the bias in member 322. For low back-pressure applications, such as occurs in making an IAP measurement, bypass valve portion 319 acts as a check valve.

Figure 9:
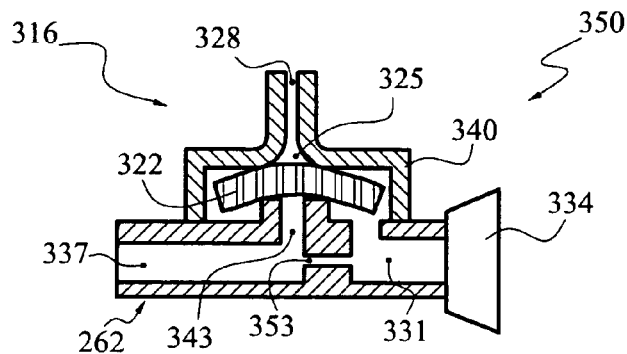
FIG. 9 is a side view, partially in section, illustrating a check/restricted-flow-bypass valve operable as a double check valve in certain embodiments of the invention.

FIG. 9 illustrates a check-bypass/restricted flow valve, generally indicated at 350. Valve 350 is structured much the same as valve 313, but also includes an additional port 353 to provide a fluid path effective to permit a low flow rate between discharge port 337 and staging area 331. Such an arrangement permits a certain amount of fluid to be removed from a remotely-actuated hydraulically operated valve, effective to assist in returning that valve to a drain configuration. Flow through conduit 225 of such removed fluid is indicated by arrow 356 in FIG. 5.

Currently, it is desired to include a check-bypass/restricted flow valve 350 in plumbing arrangements including a remotely actuatable valve 204 that is hydraulically actuated in both directions, between a drain configuration and an infusion configuration. However, it is within contemplation that certain remotely actuatable valves 250 can operate as an equivalent to a check valve component of valve 202. In such case, a simple check valve could be installed in place of valve 202 illustrated in FIG. 5. The replacement check valve would be installed in-circuit to permit flow from the fluid source 104 in a direction toward the cyclic pump.

FIGS. 10 through 13 illustrate certain functional details of an operable remotely actuatable hydraulic urine valve, generally indicated at 360. Valve 360 includes a piston 362 carried inside housing 364. Piston 362 includes piston sleeve 366 carrying an affixed end cap 368. Resilient element 370 (if present) is conveniently trapped by assembly of cap 368 and sleeve 366 effective to bias piston 362 away from an infusion configuration (illustrated in FIG. 11) and toward a draining configuration (illustrated in FIG. 10). At a draining configuration, urine, or other fluids, entering drain entrance port 372 may freely flow through valve 360 and out of drain exit port 374. Housing cap 376 is typically permanently affixed to housing 364 after the piston 362 is installed in housing 364.

As indicated in the preceding paragraph, resilient element 370 is not required for operation of a remotely actuatable hydraulic urine valve 360. In certain instances, a resilient element may be provided operable to urge piston 362 only a portion of the distance between an infusion configuration and a draining configuration. In other embodiments of a valve 360, a resilient element 370 may be provided that is operable to urge displacement of piston 362 over the entire distance from an infusion configuration to a draining configuration. Resilient element 370 may be a spring, as illustrated, or some other compressible component, such as a section of elastic tubing. In an alternative construction, it is within contemplation for a resilient element 370 to be disposed to act between distal face 377 of piston 362 and housing cap 376.

The interior of housing 364 may be regarded as defining a drain subchamber 378 and an infusion subchamber 380 that are separated by piston 362 and sliding seal element 381. Desirably, seal element 381 is arranged as a wiping seal operable to assist in maintaining at least reasonable cleanliness in the infusion subchamber 380. During operation of valve 360, fluid entering through infusion port 382 fills and enlarges infusion chamber 380, effective to displace piston 362 distally toward cap 376. Eventually, piston 362 is displaced sufficiently to engage seal surface 384 and seal element 386 (e.g. an O-ring) carried by cap 376. At that position, a fluid flow path through conduit 372 toward drain exit port 374 is occluded.

It should be understood that FIGS. 10-14 are illustrative of the working principles of one embodiment of a hydraulically actuated valve 360. Such illustrations are simplified, to increase clarity of certain illustrated structure, and to promote clarity of a description of operation of the valve. For example, structure encompassed in certain ports, such as infusion port 382, drain entrance port 372, and drain exit port 374, and not illustrated, may include connection structure adapted to interface with conduit structure, or other components of the IAP system.

Figure 11:
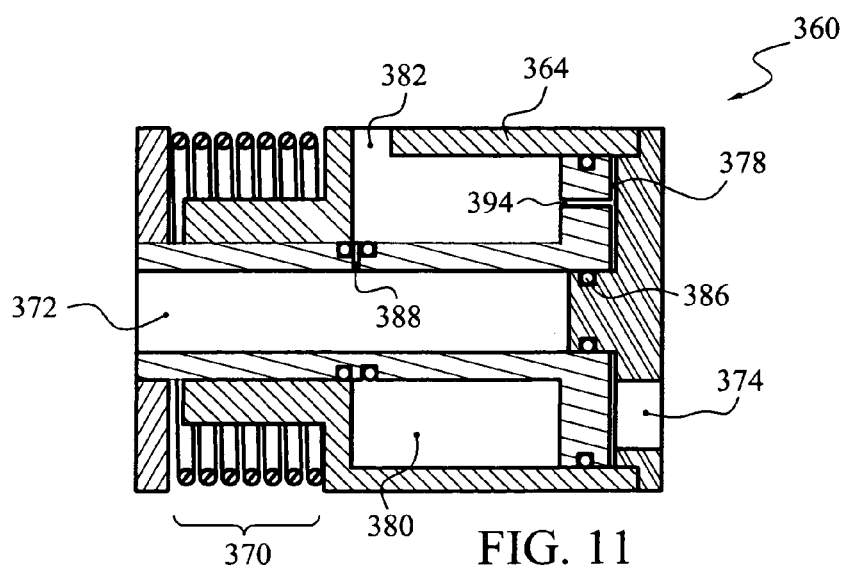
FIG. 11 is a cross-section view in elevation through a plane passing through a centerline of the urine valve illustrated in FIG. 10, with the valve shown in bladder filling configuration.
Figure 12:
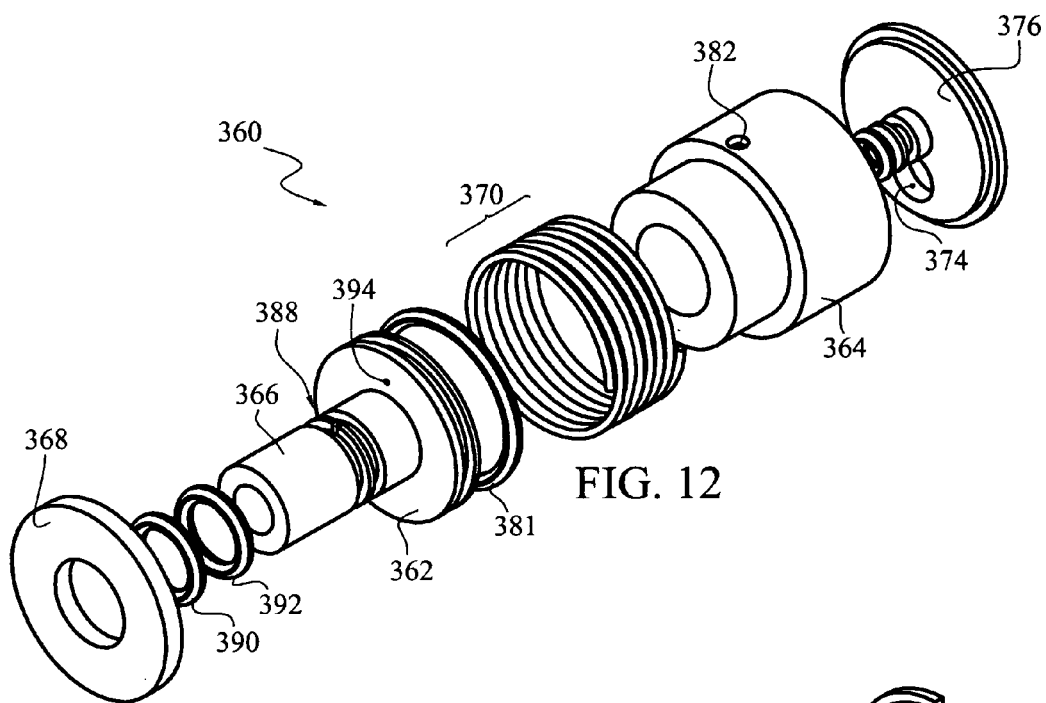
FIG. 12 is a exploded assembly view in perspective from a proximal end of the urine valve illustrated in FIG. 10.
Figure 13:
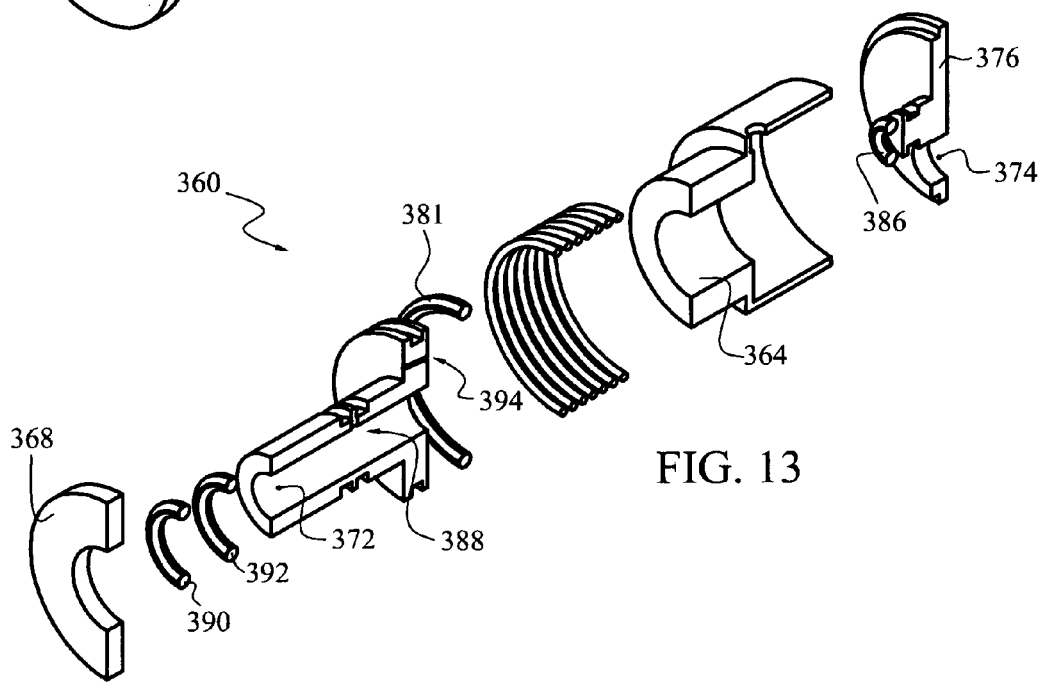
FIG. 13 is a sectional exploded assembly view in perspective of the urine valve illustrated in FIG. 10.
Figure 14:
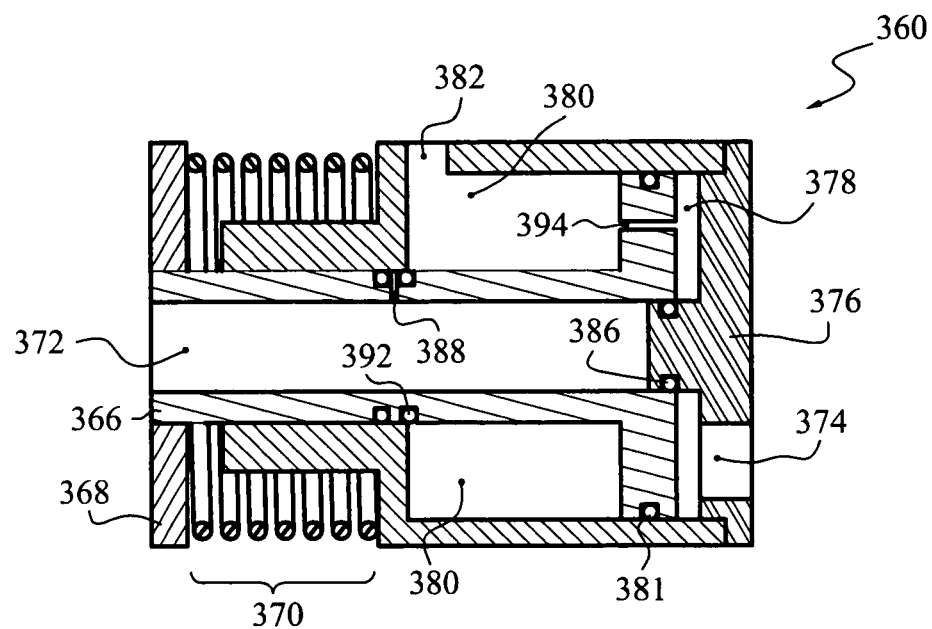
FIG. 14 is a cross-section view in elevation through a plane passing through a centerline of the urine valve illustrated in FIG. 10, with the valve shown in bladder pressure measuring configuration.

Typically, piston 362 must be displaced by an additional amount, beyond the point of first drain occlusion, to place bypass port 388 into fluid communication with infusion subchamber 380. Such an additionally displaced configuration is referred to as an infusion configuration, and is illustrated in FIG. 11. When valve 360 is placed into the infusion configuration, additional fluid passing through infusion port 382 will be directed through drain entrance port 372 and toward a patient's bladder 216 along flow path 253 (see FIG. 5). One or more bypass port 388 may be provided spaced apart around a circumference of piston sleeve 366.

Desirably, valve 360 is configured to occlude a flow path through bypass port 388, substantially automatically, when an infusing fluid flow through infusion port 382 terminates. Such occlusion resists a back-wash fluid flow into the infusion subchamber to reduce chance of contamination in a fluid supply conduit 225. One operable construction to effect such occlusion of bypass port 388 is best illustrated with reference to FIGS. 11 and 14. First bypass seal 390 and second bypass seal 392 are arranged in harmony with bypass port 388 such that a sufficiently reduced fluid pressure at infusion port 382 permits spring 370 to displace piston 362 operably for a portion of housing 364 to occlude the entrance to bypass port 388. Fluid present in the infusion subchamber 380 simply drains through bypass port 388 as piston 362 displaces under the urging of the resilient member 370. Additional fluid flow from the infusion chamber 380 through bypass port 388 is resisted once the bypass port 388 is occluded by structure of housing 364. A pressure measurement configuration (see FIG. 14) for the valve 360 may be defined as being produced when the piston 362 is disposed between a first occluding position for bypass port 388 and a first opening of the occlusion formed between seal 386 and bore surface 384.

Figure 10:
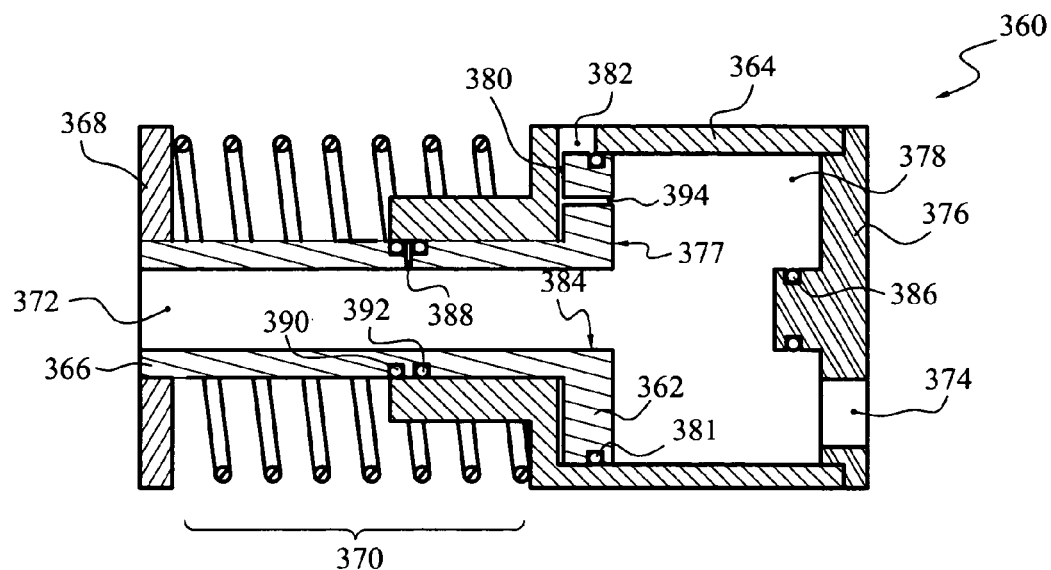
FIG. 10 is a cross-section view in elevation through a plane passing through a centerline of an operable remote-control urine valve, with the valve shown in bladder draining configuration.

A valve 360, structured as described thus far and even without a resilient element 370, would be hydraulically operable between a draining configuration and an infusion configuration. Actuation from draining to infusion configurations, and back again, could be controlled entirely by pressure and fluid flow generated by a pumping device, such as a syringe. Withdrawing sufficient fluid from the infusion subchamber 380 (e.g. along path 356 in FIG. 5) would displace piston 362 toward the left (proximally), as illustrated in FIG. 10, placing the valve 360 into a draining configuration. Such a valve may be characterized as being fully hydraulic.

With reference again to FIG. 5, when valve 250 is embodied as a fully hydraulic valve, it is generally desirable to replace illustrated syringe 116' with a syringe structured similarly to syringe 212, illustrated in FIG. 3. The replacement syringe desirably has sufficient capacity to provide the desired bolus of infusion fluid to effect an IAP measurement in a single stroke. The plunger of the loaded syringe is depressed to infuse the patient's bladder, and left in the depressed position until the pressure measurement is made. Then, the plunger is retracted to open the valve 250 and also reload the plunger with the next bolus of infusion fluid.

The amount of fluid to open a fully hydraulic valve 250 desirably is small, perhaps less than about 3 ml., so flow indicated by arrow 356 is correspondingly small. A single check valve may be used to form a portion of a flow device 202, to permit the syringe to extract fluid from the valve 250. Once valve 250 is fully opened, it can act as a check valve component of an equivalent flow control device 202. Alternatively, a check-bypass/restricted flow valve, such as valve 350, may be used as a flow control device 202.

Referring again to FIGS. 10-14, it is sometimes desirable to provide a remotely actuatable valve 360 with a substantially autonomic closing capability. By autonomic closing capability, it is meant that a valve element would be displaced from an infusion configuration to a draining configuration without requiring further user input. However, in an apparatus arranged to infer a patient's IAP, it is desirable also to provide a time interval during which the valve remains occluded to permit a pressure measurement to be made prior to placing the valve into draining configuration.

One structural arrangement operable to effect such a time-delayed autonomic closing is included in illustrated valve 360. The autonomic time-delay structure includes bleed-down port 394. Bleed-down port 394 is sized to provide a restricted fluid-flow path between infusion subchamber 380 and drain subchamber 378. A diameter of port 394 may be sized in harmony with a volume of fluid trapped in subchamber 380, and with a displacing force provided by resilient element 370, such that a desired time interval transpires as piston 362 is slowly displaced from a fluid trapping position to a draining configuration. A desirable time interval, in which to effect a pressure measurement to infer IAP, is currently believed to be about 20-30 seconds.

It currently is currently preferred for a urine valve to maintain a "smooth" or "blunt" contact area, at a potential patient interface, when actuated to either pressure measurement or fluid draining configurations. Also, indicator structures, if present, desirably have a relatively low profile to avoid inflicting patient discomfort if brought into contact with the patient's leg.

Certain remotely actuated valves benefit from the presence of indicia to show the current flow path through the valve. Such indicia may assist in diagnosing possible causes of unexpected pressure readings. In rotationally-activated hydraulic valve 222 (see FIGS. 3,4) an indicator 466 is placed into axial agreement with alignment indicator 468 when valve 222 is oriented in a drain configuration. Indicators 466, 468 may protrude slightly from a surface of housings portions of valve 222 to provide both tactile and visual feedback to a valve operator. Such indicators are only one example able to provide visual feedback for a health practitioner to verify return of a urine valve to a drain configuration.

It is within contemplation to form a piston 362, or other element operable as a valve gate, that is visible (e.g. through a transparent housing 364 (see FIGS. 10-13)) to alternatively, or additionally, indicate a valve flow path setting. It is further within contemplation to provide written indicia to spell out a flow path corresponding to a particular valve orientation. It is also within contemplation to provide remote a manual override effective to manually fix a "stuck" valve.

Figure 15:
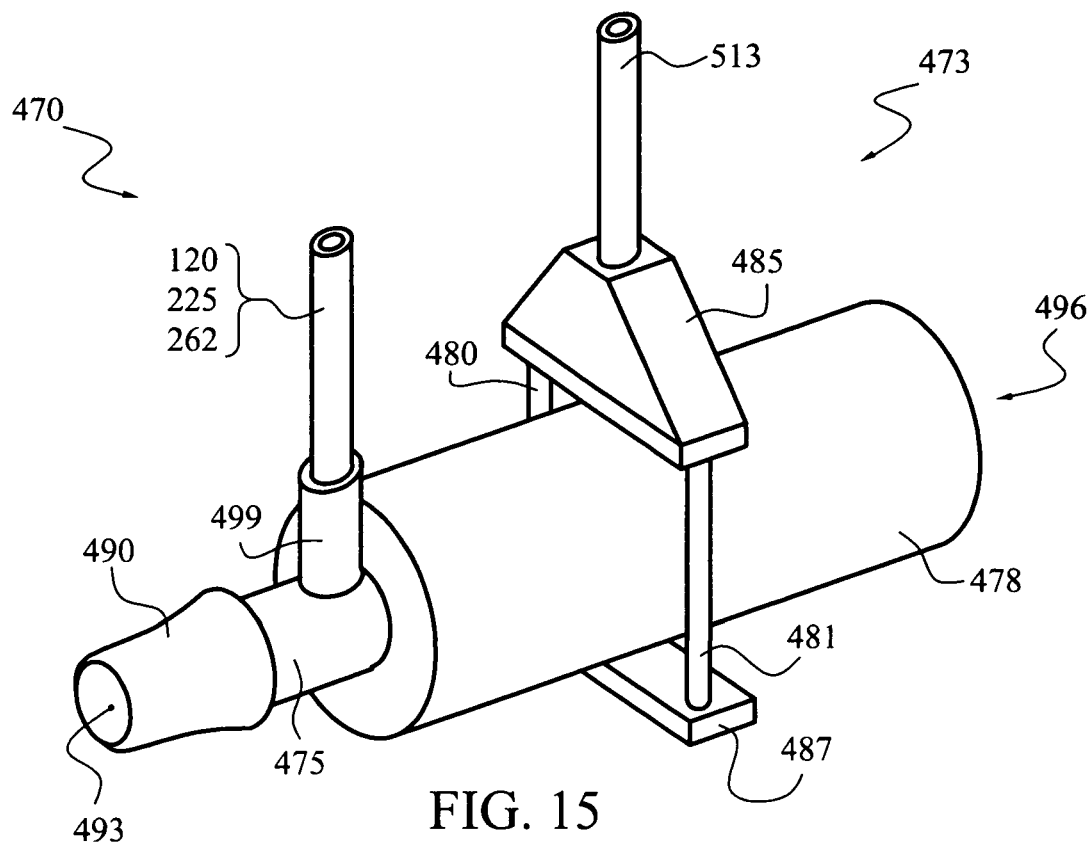
FIG. 15 is a view in perspective of an alternative valve arrangement effective to occlude a urine drain conduit under control of an operator located remote from the drain conduit.
Figure 16:
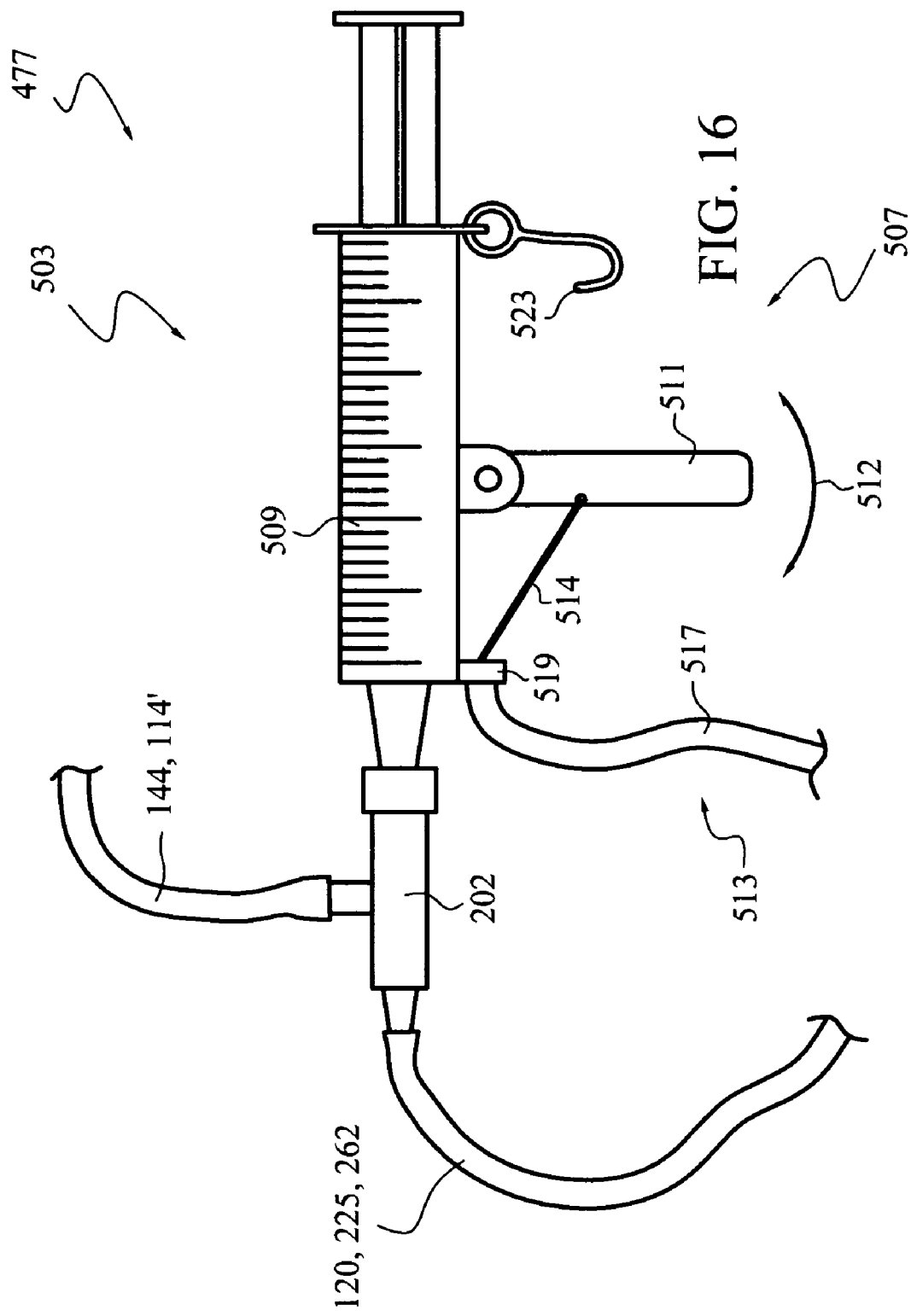
FIG. 16 is a view in perspective of one conveniently arranged dual-purpose remote-control device operable to actuate the valve of FIG. 15, and also to infuse fluid into a patient's bladder
Figure 17:
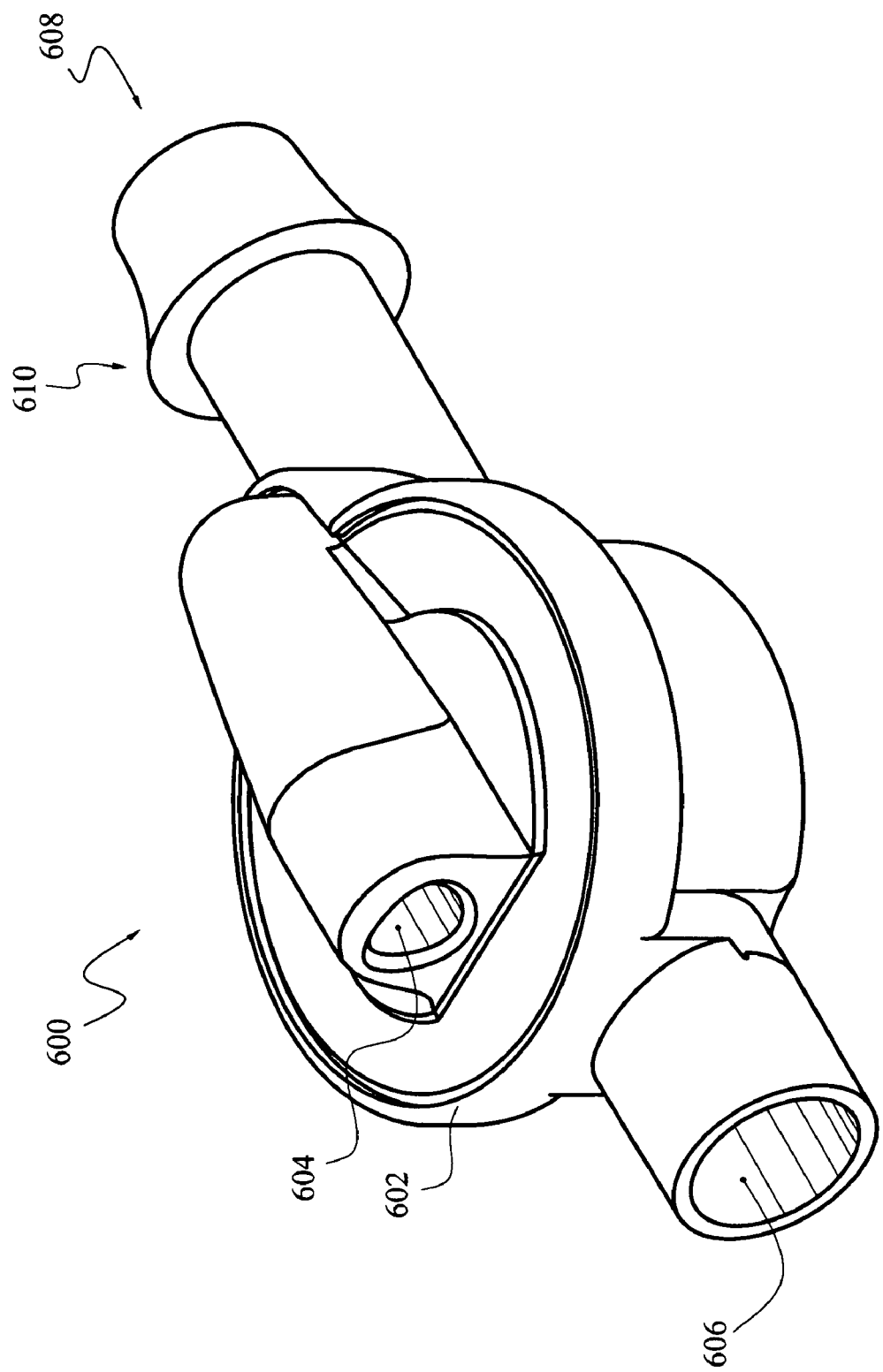
FIG. 17 is a view in perspective of a currently preferred hydraulically actuated valve.

FIGS. 15 and 16 illustrate an alternative assembly 470 effective to permit occlusion of a urine drain path and infusion of fluids into a patient's bladder under control of personnel located at a convenient and remote location. Assembly 470 includes a remotely actuated valve generally indicated at 473, coupling conduit 475, and an actuator assembly generally indicated at 477. Assembly 470 may be installed in-circuit as illustrated in any of FIGS. 2-5, in replacement of corresponding structure.

Illustrated valve 473 is a conduit clamp-style valve that may be actuated between draining and occluding configurations mechanically, as illustrated. Such clamp-style valves typically provide simplicity, low cost, and reliability in maintaining a sterile field inside conduit structure during extended use of an IAP apparatus. In certain alternative construction, a clamp-style valve 473 may be operated hydraulically, or by an electro-mechanical device, such as a solenoid driven clamp arrangement. In certain less desirable embodiments of the invention, it is within contemplation to configure a remotely actuated valve 473 as a cable-actuated gate valve.

It is preferred for a valve 473 to be maintained in association with flexible conduit member 478, to ensure reliable operation. Illustrated valve 473 includes a pair of actuating cables 480, 481, effective to maintain valve 473 in position along an axis of conduit 478. Cables 480, 481 are retracted to clamp and occlude tube 478 between top gate member 485 and bottom gate member 487. It is important also to ensure clamp valve 473 remains in position to squeeze a transversely manipulatable portion of the conduit 478 (e.g. a section not reinforced by a portion of conduit connector 475). Sometimes, axial protrusions (not illustrated) are provided to resist axial migration of valve 473 with respect to tube 478. Alternatively, one or more of top gate 485 and bottom gate 487 may be affixed to tubing section 478. Of course, other arrangements (not illustrated), of known clamp-type conduit valves are operable in alternative embodiments of the invention.

With reference to FIG. 15, coupling conduit 475 is adapted at barbed proximal end 490 to engage through-bore 493 in fluid communication with a discharge end of a catheter 102. A fluid-tight connection at proximal end 490 may be made directly with such catheter 102, or may include intermediate conduit structure. One arrangement of intermediate structure is illustrated in FIG. 5, and is operable to place pressure transducer 218 substantially in isolation from pressure spikes associated with pumping of infusion fluids into the bladder 216. Distal connection end 496 of tubing 478 provides coupling structure effective to place through-bore 493 in fluid communication with a drain receptacle, such as bag 224 in FIG. 3. Desirably, coupling conduit 475 includes a connection structure 499, operable to place an infusion conduit (e.g. 120, 225, 262) in fluid communication with through-bore 493.

Connection structure 499 may be configured to receive any desired cooperating connection device, as dictated by the fluid circuit assembly. For example, it is within contemplation for connector 499 to be nonexclusively embodied as a urine collection/aspiration port adapted to receive an infusion needle 122; as a simple 'T' intersection; or as a luer-activated sample port. Connector 499 may also be associated with a check valve to resist migration of fluids discharged from the bladder in an "upstream" direction into an infusion conduit.

FIG. 16 illustrates one workable actuator assembly 477 operable to remotely control valve 473, and also to infuse fluids into a patient's bladder 216. Assembly 477 includes a dual function syringe, generally indicated at 503. Syringe 503 includes a valve actuation assembly, generally indicated at 507, and an integral infusion syringe portion 509. Syringe portion 509 may be structured in accordance with known syringes, including any of the embodiments illustrated in FIGS. 1-5. For convenience, syringe portion 509 and valve actuator portion 507 are integrated as a single assembly. It is within contemplation also to provide each actuator portion as a separate component. However, it is currently believed to be more convenient (e.g. to an anesthesiologist), to combine the control apparatus into a single assembly to reduce clutter in an operatory.

Valve actuation assembly 507 includes a pivoting lever actuator, or handle 511. Handle 511 may conveniently be mounted for pivotal rotation, indicated by arrow 512, with respect to syringe 509 in a working relationship with a control cable, generally indicated at 513. An orientation of handle 511 may provide feedback indicating a configuration of a remotely actuated valve—occluding or draining. Handle 511 is affixed to an end of cable element 514, and control cable sheath 517 abuts holding structure 519. Therefore, rotation of handle 511 is effective to extract or replace a section of cable element 514 from or into cable sheath 517. Cable element 514 operates on cables 480 and 481 to move gate 487. Biasing structure (not illustrated) may be provided to urge gate 487 toward a draining configuration, in the event that a sufficient restoring force is not supplied by tubing 478. Keeper structure, such as illustrated keeper hook 523, may be provided to hold handle 511 in position effective to maintain a remote valve in a drain occluding configuration during a pressure measurement interval. Alternative keeper structures within contemplation nonexclusively include: ratchet assemblies, friction interfaces, and toggle-action mechanisms.

FIGS. 17-22 illustrate details of construction of another currently preferred valve, generally indicated at 600, operable as a urine valve in an assembly adapted to monitor a patient's LAP in a medical setting. Desirably, the housing 602 of valve 600 is small in size, and configured to provide a blunt contact interface, to reduce intrusiveness of the valve 600 in an installed location at a patient's groin area. A workable embodiment of housing 602 is less than about 3 cm in diameter, and about 1 cm deep.

Valve 600 is adapted for hydraulic actuation through control port 604. Such hydraulic actuation permits control of fluid flow through the valve from a convenient location that may be remote from the valve. Furthermore, valve 600 is adapted to provide at least one occludable normally-open, fluid flow path between drain port 606 and entrance port 608. It is currently preferred to attach a pig tail piece of control fluid conduit to control port 604 using an adhesive bonding technique. However, it is also workable to provide a barb-type connector structure as an alternative.

Similarly, conduit connection structure carried in association with ports 606 and 608 may be arranged to receive conduit or tubing for a slip-on installation, as illustrated, or in an alternative plug-fit, threaded engagement, or adhesively attached arrangement. Drain port 606 is not expected to see significant fluid pressure when used to measure IAP, since it generally drains to atmospheric pressure. Therefore, a smooth, slip-on connection is generally deemed adequate to maintain fluid communication between the valve 600 and a drain container. A barb fitting, generally indicated at 610 in FIG. 17, or some other conduit-connecting structure, typically is included at entrance port 608 to resist decoupling the valve 600 from fluid communication with a catheter 102. In certain cases, an additional clamp (such as a hose clamp, not illustrated), may be included to further secure engagement between a fluid carrying conduit and a barb fitting.

Figure 18:
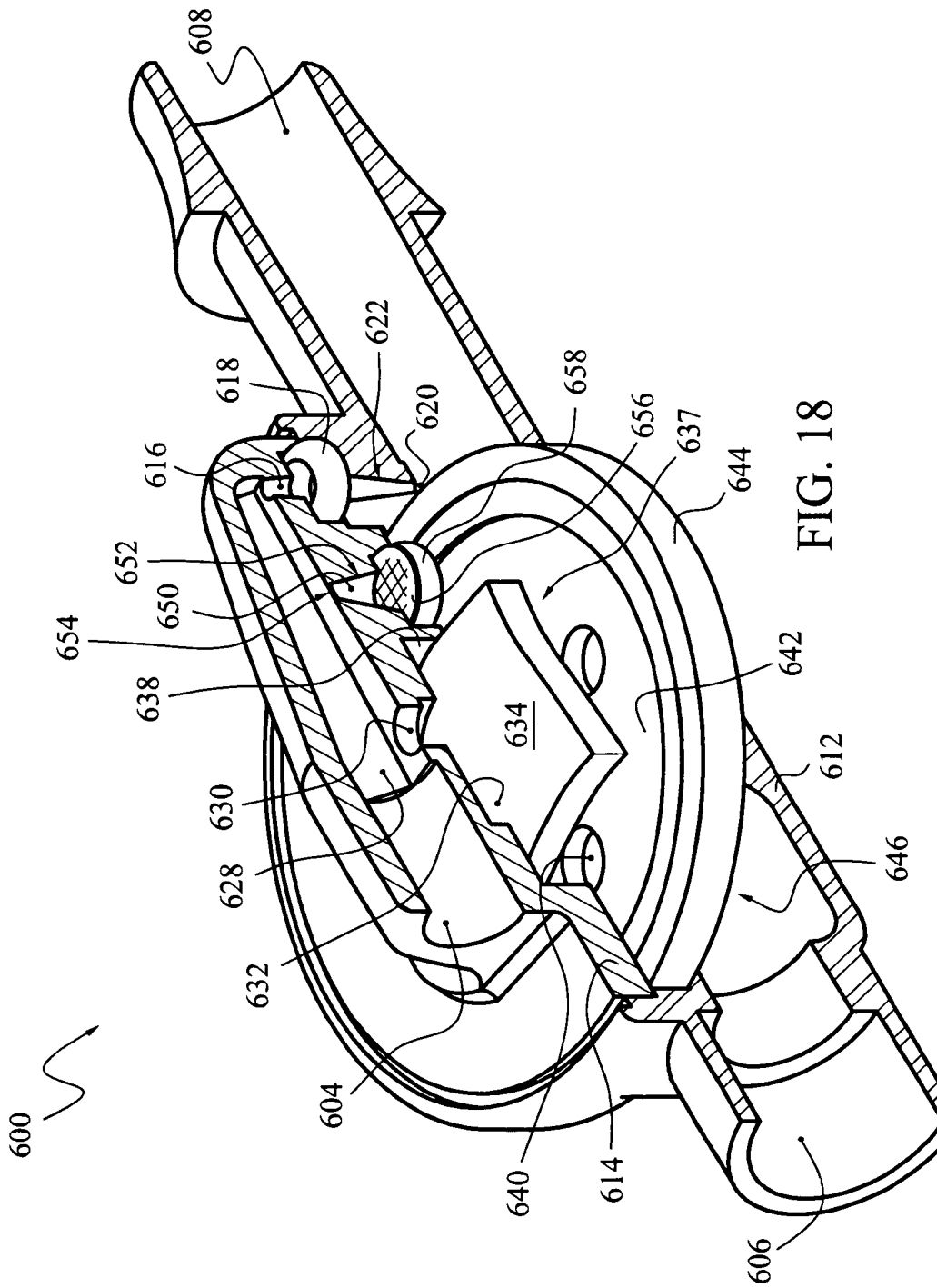
FIG. 18 is a view in perspective, partially in section, of the valve illustrated in FIG. 17.

With reference to FIG. 18, valve housing 602 includes a body 612 and a closure 614. It is currently preferred to bond the closure 614 to body 612 using an adhesive, such as an ultraviolet cured adhesive. O-ring 618 is included as a safety seal to resist leakage from the fluid conduit extending between control port 604 and entrance port 608. O-ring 618 also helps ensure that adhesive used to assemble the housing 602 does not occlude fluid flow from bolus port 616 through the orifice 620 of the fluid-flow restriction valve generally indicated at 622. As illustrated, bolus port 616 is placed in fluid communication with control port 604 by way of lumen 628.

Lumen 628 also places control port 604 in fluid communication with actuation port 630. Flow restriction valve 622 is relied upon to generate a back pressure in excess of about 1-½ psig. A portion of fluid entering control port 604 may therefore flow through actuation port 630, and into a chamber 632 sealed by resilient flap seal element 634. Seal element 634 is biased by post 636 (see FIG. 19) to form a check valve portion, generally indicated at 637, of valve 600. Illustrated check valve 637 is configured similarly to the valve 316 illustrated in FIG. 7, although a check valve having other construction would be operable. Seal member 634 resists fluid flow between chamber 632 and chamber 638. Fluid in chamber 638 is free to flow through one or more apertures 640 passing through support disk 642. Disk 642 provides a support foundation for an expandable diaphragm 644 that is configured and arranged to operate as a seal element to control fluid communication between draining port 606 and entrance port 608. When sufficiently inflated, diaphragm 644 engages cooperating structure of body 612 effective to close a control valve portion, generally indicated at 646, of valve 600. Fluid flowing through aperture 640 either inflates or deflates diaphragm 644, and can open or close the valve 600.

As diaphragm 644 is deflating, fluid flows into chamber 650 of the bleed-down valve portion, generally indicated at 652, of valve 600. Chamber 650 is placed in fluid communication with lumen 628 by way of a small aperture, generally indicated at 654. The small aperture 654 has an opening area sized to permit a restricted fluid flow rate between the chamber 650 and lumen 628. The size of the opening 654 is selected in harmony with a resilience of diaphragm 644 and viscosity of the working fluid to provide a desired bleed-down fluid flow rate for valve 646. In a workable embodiment of valve 600 adapted to operate with saline solution, the diameter of opening 654 is about 0.05 mm (0.002 inches), and the diameter of opening 620 is about 0.5 mm (0.020 inches). The resilience of diaphragm 644 provides a working pressure to urge bleed-down fluid flow through aperture 654. A time delay in opening of control valve portion 646 may then be determined by the volume of working fluid that must pass through aperture 654 before the seal formed by control valve 646 is broken, and valve 600 is opened.

Because the aperture 654 in a currently preferred embodiment is very small, it is prone to occlusion by debris carried in the bleed-down fluid. In such case, it is preferred to dispose a screen 656 upstream of chamber 650 to resist passage of any such occluding debris. A workable screen having apertures on the order of 0.01 mm (0.0004 inches) has been determined to be formable from polyester mesh. Advantageously, screen 656 may be held in place by an O-ring 658 that can also form a sealed perimeter around the screen to resist fluid and debris leaking past the screen and into chamber 650.

Figure 19:
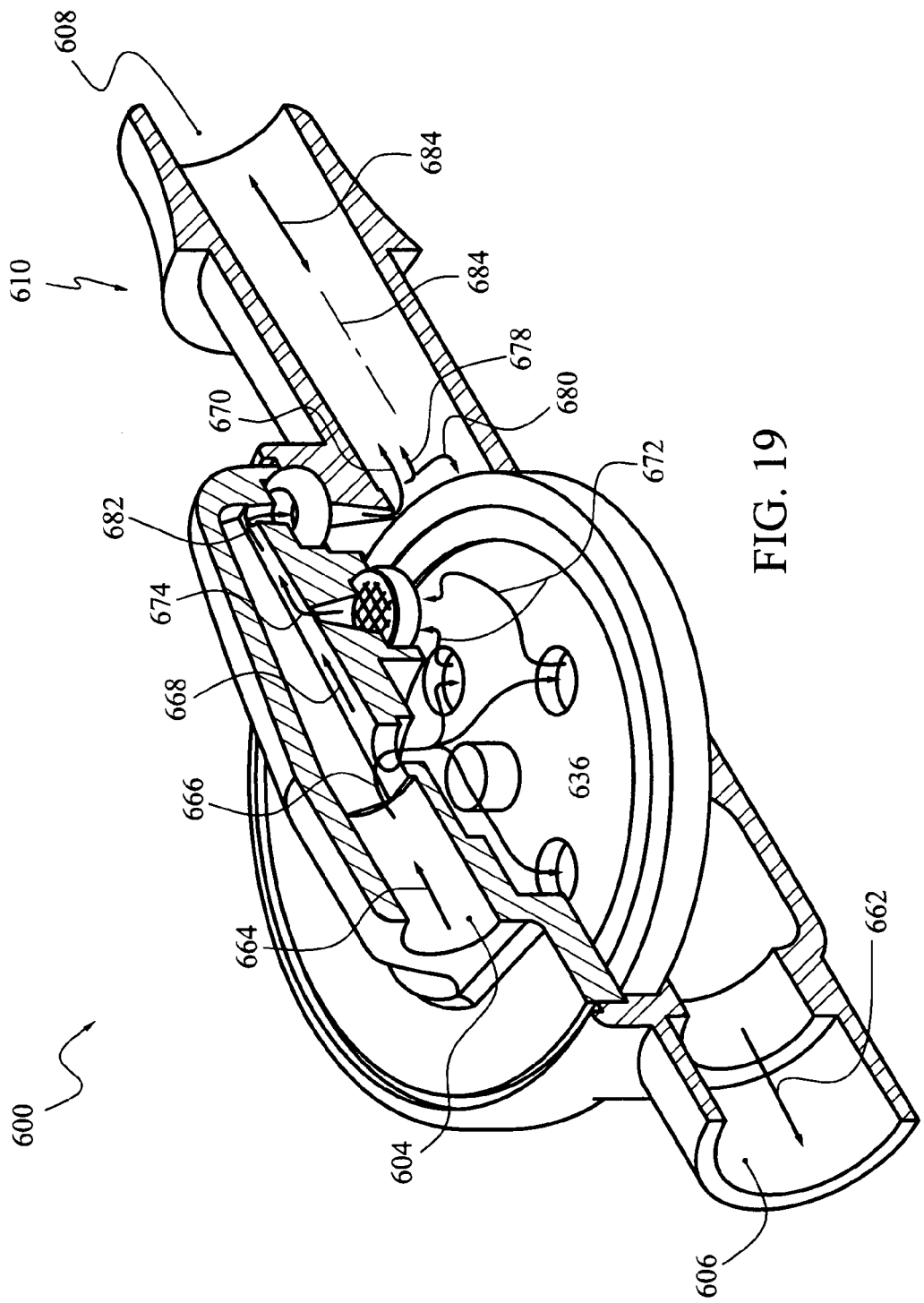
FIG. 19 is a view in perspective, partially in section, of the valve illustrated in FIG. 17, with a valve seal removed for illustrative purpose.
Figure 20:
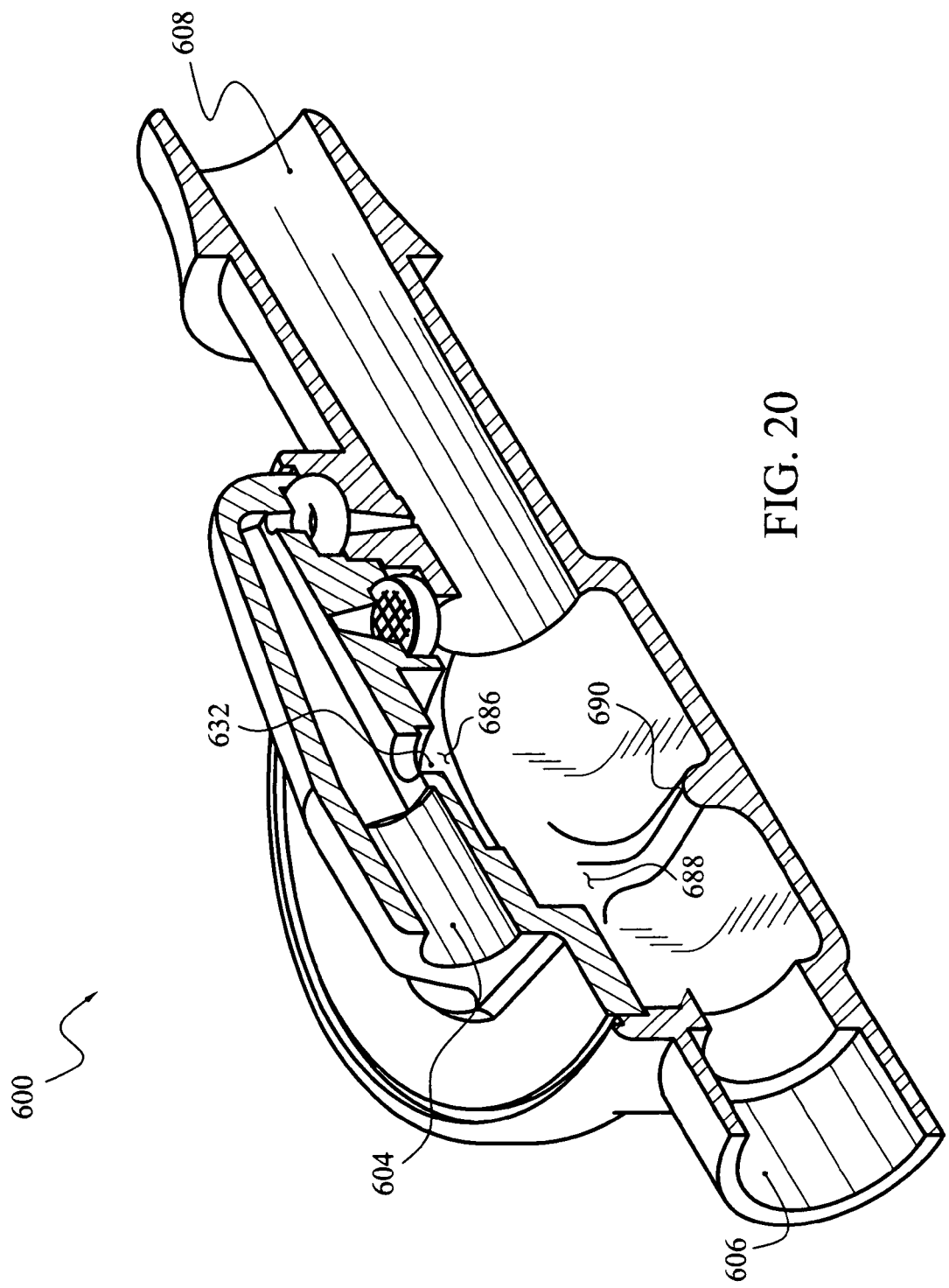
FIG. 20 is a view in perspective, partially in section, of the valve illustrated in FIG. 17, with additional internal components removed for illustrative purpose.
Figure 21:
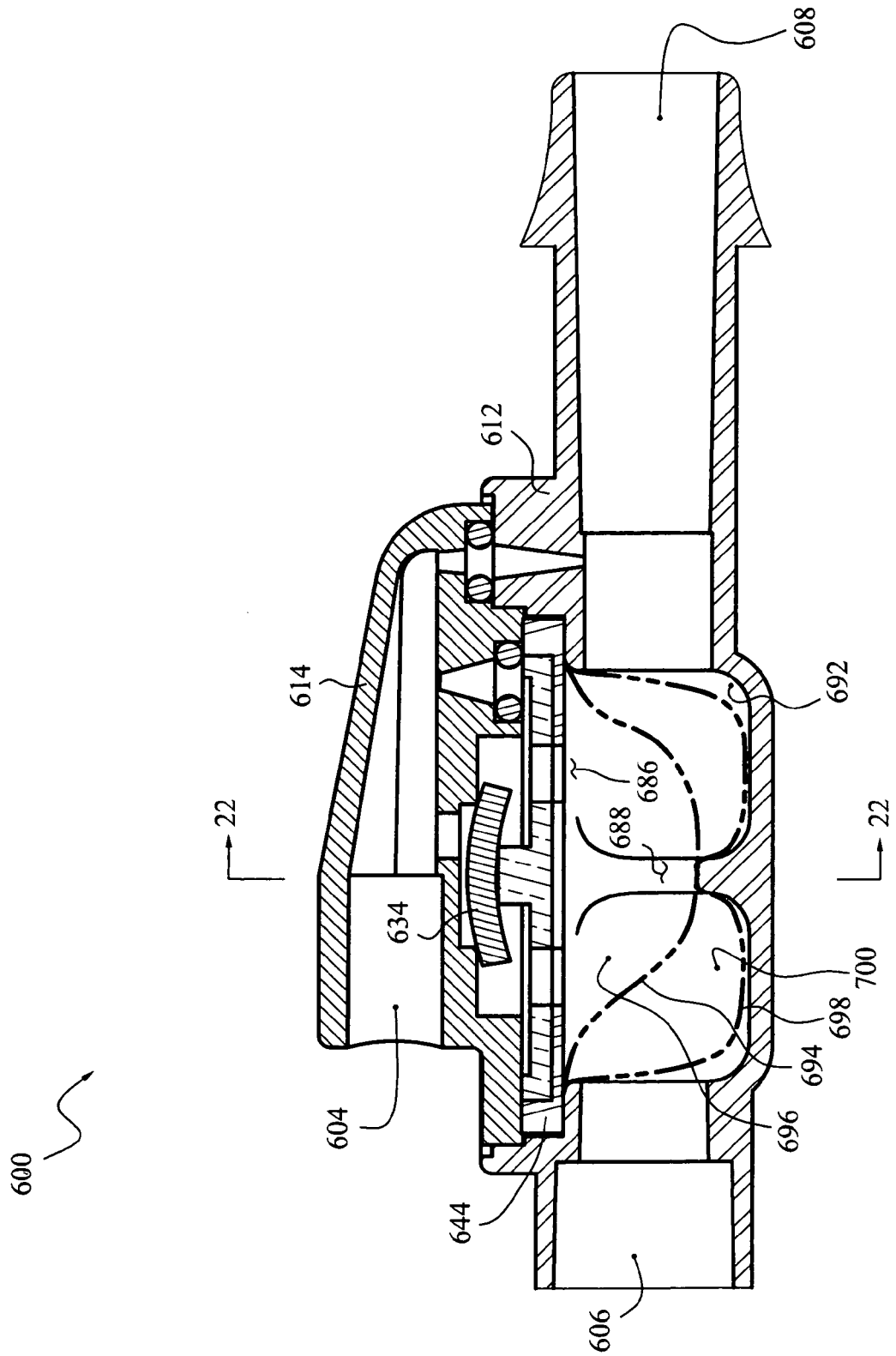
FIG. 21 is a side view, partially in section, of the valve illustrated in FIG. 17.
Figure 22:
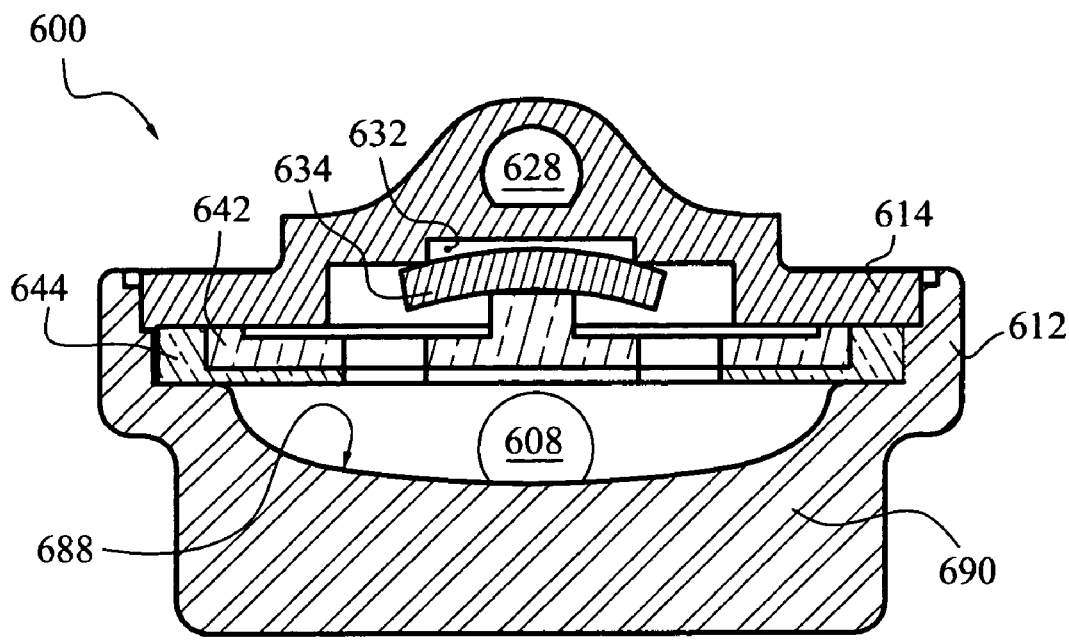
FIG. 22 is a view taken through section 22-22 in FIG. 21, and looking in the direction of the arrows.

Fluid flow through the valve 600 will now be described with particular reference to FIGS. 2 and 19. For convenience of description, valve 600 will be described as being installed in an assembly to measure a medical patient's IAP. However, it is recognized that valve 600 may be used in other situations. Valve 600 may be used in place of valve 204 in an assembly having a plumbing arrangement similar to that indicated in FIG. 2. The effect on measured values indicated by a pressure transducer 121 during infusion of the bladder (not indicating real-time bladder pressure) is deemed acceptable for the tradeoff of accomplishing a simplified configuration of plumbing conduits, and corresponding reduction in likelihood of error by clinicians.

Valve 600 is a normally-open valve, structured to permit draining fluid flow, indicated by arrow 662, through drain port 604. Injected fluid flow, indicated at arrow 664, typically is caused by actuation of a cyclic pump device, such as a syringe 116'. Desirably, injected fluid 664 flows at an approximately constant rate sufficient to generate an operational back-pressure upstream of flow restriction valve 622. Such flow rate is typically accomplished by conventional manual actuation of a plunger of a syringe. A sufficient operational injected flow rate in one embodiment of a valve 600 is about 4 ml/sec. Cyclic operation of an infusion pump can be accommodated by a time delay feature (described in more detail below with reference to FIG. 21) inherent in a valve 600. During actuation of valve 600, a portion of injected fluid 664 is diverted as actuation fluid flow, indicated by multi-headed arrow 666, and inflates the diaphragm 644 to close a flow path between entrance port 608 and drain port 606.

While the valve 600 is closing, which desirably requires injection of perhaps only 1 to a few ml of working fluid, a portion of the injected fluid flow 664 travels toward the flow restriction valve 622, as indicated at arrow 668. After the valve 600 is fully actuated, all of injected fluid flow 664 continues as bolus fluid flow, indicated by arrow 670, and passes through flow restriction valve 622. Bolus fluid flow 670 continues until the desired amount of fluid is delivered to the patient's bladder, and injection fluid flow 664 is terminated.

Once injection fluid flow 664 is terminated, working fluid trapped by diaphragm 644 is free to flow from aperture(s) 654, as indicated by arrows 672, toward bleed-down valve 652. The flow rate of bleed-down fluid flow indicated by arrow 674 is determined, in-part, by the size of the bleed-down orifice 654, which can be significantly smaller than the orifice 620 of flow restriction valve 622. A human bladder expands to accommodate such slow bleed-down fluid flow 674 without causing any significant back pressure. At the low flow rate typically inherent in bleed-down flow 674 of the illustrated embodiment 600, no significant pressure drop is developed by bleed-down fluid passing through the flow restriction valve 622. Therefore, bleed-down fluid flow in illustrated valve 600 is virtually unimpeded as it passes through flow restriction valve 622 and initially flows toward the patient's bladder, as indicated by arrow 678, so pressure in the lumen 628 reflects substantially real-time bladder pressure.

Because there is no significant pressure drop associated with fluid flow through lumen 628 during bleed-down flow 674, pressure measured upstream of control port 604 (e.g. at a pressure transducer 121), substantially reflects bladder pressure in real-time. Therefore, the pressure measurements made during a period of bleed-down flow 674 may be used to infer the patient's IAP. Desirably, a urine valve, such as valve 600, is configured to cause bleed-down flow over an increment of time sufficient to obtain a stable pressure measurement of the patient's bladder pressure. It has been determined that an increment of time of about 20-30 seconds is adequate for such purpose.

Sometimes, injected fluid flow 664 may be characterized as control fluid flow. Injected fluid flow encompasses actuation fluid, and bolus fluid. Fluid flow through fluid-flow restriction valve 622, indicated by arrow 682, can at different times encompass the portion of injected fluid 668, bolus flow 670, or bleed-down flow 674. Once sufficient working fluid is evacuated from confinement by diaphragm 644 by way of bleed-down fluid flow 674, valve 600 opens, and additional bleed-down fluid can flow toward drain port 606, as indicated by arrow 680, along with fluid draining from the bladder. Once the draining path through valve 600 is opened, pressure in the patient's bladder quickly drops to approximately atmospheric pressure as fluid in the bladder is drained. Arrow 684 has been illustrated as having two heads in recognition that flow at the entrance port 608 can be directed either to enter, or to exit, the valve 600.

Details of the valve-closing seal arrangement formed between diaphragm 644 and seal structure carried by body 612 will now be described with particular reference to FIGS. 20 through 23. It is believed that the hydraulically-transverse actuation of the diaphragm 644 employed in illustrated valve 600 represents a novel way to occlude a drain path through a conduit. Membrane 644 of illustrated valve 600 forms a portion of a fluid-confining boundary, inside of which boundary fluid flows through valve 600. In that respect, membrane 644 provides a dual-function wall portion of the conduit inside of which fluid flows through valve 600.

Membrane 644 may be regarded as a moving wall, which can be displaced toward a fixed wall to occlude a draining path, indicated by centerline 684 (see FIG. 19) through valve 600. Membrane 644 can therefore be regarded as providing a traveling flow boundary with its direction of motion being directed generally transverse to flow through the valve 600. In contrast to a valve having a seal element such as a balloon-in-a-pipe, hydraulic displacement of the membrane 644 to close the valve actually reduces the size of a cross-section through the flow conduit, or lumen, at the seal area.

Body 612 of housing 602 provides the fixed wall portion against which membrane 644 is forced effective to occlude valve 600. A fluid resistant seal is formed in illustrated valve 600 between membrane 644 and rim surface 686 during manufacture and assembly of the valve 600. Rim surface 686 circumscribes a perimeter of membrane 644. The circumferential seal between rim 686 and membrane 644 is in effect during both valve-open and valve-closed operation. When the valve 600 is closed, membrane 644 is distended to also contact surface 688 extending along a top portion of transverse rib 690. Membrane 644 may be regarded as providing a traveling wall. Surface 688 may be regarded as a fixed structure against which the traveling wall of membrane 644 is urged to form a seal to resist draining fluid flow. Contact between surface 688 and membrane 644 forms a seal that works in harmony with a portion of the circumferential seal to resist draining fluid flow through valve 600.

Transverse rib 690 is shaped somewhat like a saddle and is effective to partially subdivide the expansion chamber 692 into which membrane 644 is inflated. Rib 690 represents one convenient embodiment of structure forming a portion of a draining fluid-flow resisting seal. Rib 692 also provides structure operable to produce a timing delay in automatic reopening for valve 600.

Once membrane 644 contacts the surface 688 (at the position indicated by phantom line 694 in FIG. 21), draining fluid flow along centerline 684 is occluded. The volume of working fluid trapped behind membrane 644 at such first valve-closed position is indicated at 696. The conformation of body 612 and rib 690 permits further inflation of membrane 644, to approximately the position indicated by phantom line 698, or even beyond. The additional volume of working fluid trapped behind membrane 644 at such further inflated position is indicated at 700, and sometimes is referred to as timing fluid volume, or timing volume, which must be removed from confinement behind membrane 644 before valve 600 can open. Timing volume 700 is regarded as being held in one or more timing chambers. Therefore chamber 692 may be characterized as providing one or more timing chambers in addition to valve-closing seal structure carried on a fixed wall. The size of the timing volume, the viscosity of the working fluid used to inflate or displace the membrane 644, the membrane's resilience or biasing force, and the size of the bleed-down aperture 654, all cooperate to determine the amount of time that will pass, subsequent to termination of flow of control fluid through control port 604, before the valve 600 will open to permit draining fluid flow.

Figure 23:
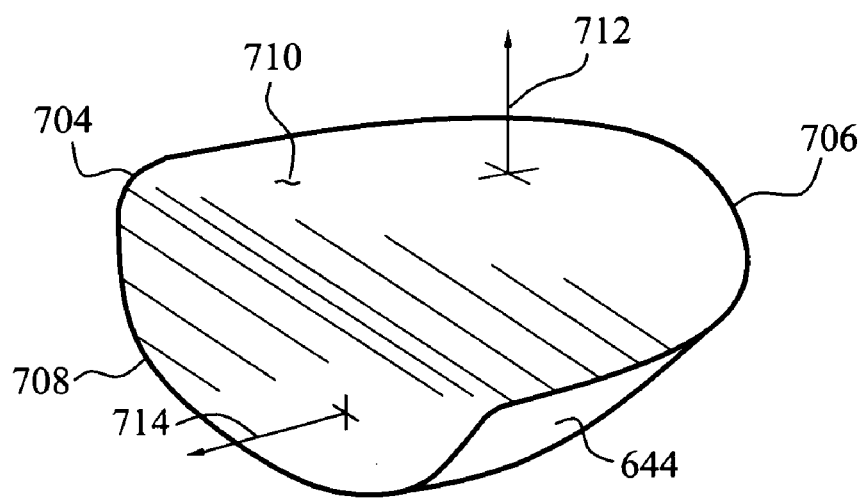
FIG. 23 illustrates a surface or area bounded at its perimeter by a wetted seal interface formed in the valve illustrated in FIG. 17.

FIG. 23 illustrates a section of membrane 644 at its distended position during first valve-closed contact with surface 688. At such position, a seal perimeter may be defined as the wetted interface, or boundary 704, at the junction line formed between fluid in chamber 692 and contact between the membrane 644 and associated sealing surfaces 686 and 688. As illustrated, wetted interface 704 includes a substantially horizontal portion 706 corresponding to the seal formed between membrane 644 and rim 686. The illustrated substantially vertical portion 708 of wetted interface 704 is formed between membrane 644 and surface 688 of rib 690.

A seal area 710 may be defined as a hypothetical construct stretching between the perimeter defined by wetted interface 704. Note that seal area 710 has a different shape than the distended membrane 644. Seal area 710 provides structure having characteristics that differentiate the valve seal in certain embodiments constructed according to principles of the instant invention over other known valves. For example, certain known valves are arranged to form seal boundaries disposed around an inside circumference of a pipe, or at the opening of round orifices. In contrast to the illustrated seal surface 710, seal areas in such known valves may be characterized as being 2-dimensional, or flat, and circular. In contrast, the illustrated seal surface 710 is convoluted, or "folded", and is therefore properly characterized as being a 3-dimensional entity. Surface 710 may be regarded as being stretched across the area bounded by a 3-dimensional perimeter. A vector 712 normal to one portion of area 710 is approximately vertical, and a vector 714 normal to another portion of area 710 is approximately horizontal. Furthermore, illustrated seal surface 710 may be characterized as being noncircular. Additionally, seal surface 710 may be characterized as including a portion disposed substantially perpendicular to a direction of unoccluded flow through the flow resisting area of valve 600, and a portion disposed nonperpendicular to, or even parallel to, such fluid flow.

A representative embodiment of a valve 600 is used in a medical setting as a portion of an assembly operable to measure a patient's IAP. Such representative valve uses saline as the control fluid (and therefore as the working, bleed-down, and bolus fluid). Approximately 1 ml of working fluid are required to first close the valve to resist draining fluid flow. The achieved timing volume (which is dependent upon control fluid pressure and flow duration), generally is on the order of about 2 ml. The diameter of the flow restriction aperture is about 0.020 inches, and the diameter of the bleed-down aperture is about 0.002 inches. An injection molded membrane seal made of 40 Durometer silicone has diameter of about 0.890 inches, and an uninflated membrane thickness of about 0.020 inches. Such representative valve provides about 60-70 seconds of delay during bleed-down, during which time the patient's bladder pressure may be measured, before automatically opening to permit draining fluid flow.

It is currently preferred, when possible, to injection mold certain valve components in straight-pull, simple molds to reduce mold-making and attendant manufacturing costs. Molded valve components may be formed from a variety of medical grade plastics, including polycarbonate, ABS, acrylic, and polyethylene. A currently preferred Polycarbonate housing material includes Dow Calibre available under part numbers 2081-15 FC030006 or 2081-15 FC030116. O-ring seals may be injection molded from suitable rubber-like materials, with 70 Durometer silicone currently being preferred. A workable inflatable membrane-like sealing diaphragm may be formed by injection molding from medical grade silicone material, such as 40 Durometer USP Class IV material sold by Dow Chemical Company under part number LSR C6-540. A variety of bonding procedures are operable to join valve components to form a valve assembly, including plastic welding techniques such as solvent, ultrasonic, friction, shear, and heat welding, as well as adhesive bonding techniques including adhesives, and particularly adhesives that are cured using ultraviolet-light.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. For example, one or more component in a particular illustration may be combined with one or more other component in one or more different illustration. The scope of the invention is, therefore, indicated by the appended claims rather than by the foregoing description. All changes which come within the meaning and range of equivalency of the claims are to be embraced within their scope.

What is claimed is:

1. A hydraulically actuated valve, comprising:
   a housing configured and arranged to permit fluid communication between an entrance port, a control port, and a drain port;
   a seal member arranged inside said housing for hydraulic actuation between a valve-open position and a valve-closed position, said valve-open position permitting draining fluid flow between said entrance port and said drain port, and said valve-closed position resisting said draining fluid flow;
   a fluid-flow restriction valve disposed in a first fluid path along which control fluid may flow in a first direction from said control port toward said entrance port, said fluid-flow restriction valve being structured to generate a back-pressure responsive to a flow of said control fluid in said first direction, said back-pressure being effective to urge flow of actuation fluid toward said seal member; and
   a bleed-down port configured and arranged to permit evacuation, as bleed-down fluid, of actuation fluid confined by said seal member; and said seal member comprises an expandable diaphragm configured and arranged to be self-biased from said valve-closed position toward said valve open position.

2. The hydraulically actuated valve of claim 1, wherein:
   subsequent to being displaced beyond a valve-closed position, said seal member is biased to urge said bleed-down fluid to flow through said bleed-down port effective to cause a time-delayed opening of said valve.

3. The hydraulically actuated valve of claim 1, wherein:
   a time-delay volume is created by displacement of said seal member to encompass a confined volume in excess of that volume required to form an initial blockage of said draining fluid flow.

4. The hydraulically actuated valve of claim 1, wherein:
   said bleed-down port is arranged to discharge said bleed-down fluid along a path that overlaps a portion of a second fluid path between said control port and said drain port.

5. The hydraulically actuated valve of claim 4, wherein:
   flow of said bleed-down fluid is directed along a third fluid path defined, in-part, between said bleed-down port and said fluid-flow restriction valve.

6. The hydraulically actuated valve of claim 1, wherein a fluid path followed by said bleed-down fluid overlaps a portion of said first fluid path.

7. The hydraulically actuated valve of claim 1, wherein:
   said first fluid path is defined, at least in-part, by structure of said housing disposed between said control port and said entrance port.

8. The hydraulically actuated valve of claim 1, wherein:
   a bleed-down valve associated with said bleed-down port is structured to cause the rate of flow of said bleed-down fluid to be sufficiently low that it does not generate a significant back-pressure when passing through said flow-restriction valve.

9. The hydraulically actuated valve of claim 1, wherein:
   said seal member comprises a membrane configured and arranged to form a traveling wall operable to collapse a cross-section of said first flow path at a seal location effective to form a fluid-flow resisting seal in cooperation with valve-closing seal structure carried by a fixed wall.

10. The hydraulically actuated valve of claim 1, wherein:
    a perimeter forming a wetted boundary to a seal area of said valve is a 3-dimensional entity.

11. The hydraulically actuated valve of claim 1, wherein:
    structure forming a seal to resist said draining fluid flow is configured and arranged such that a normal to a portion of a bounded seal area has a component oriented substantially perpendicular to a vector indicating valve-open fluid flow through the opening defined by the perimeter of the bounded seal surface.

12. A method for hydraulically actuating the valve of claim 1, said method comprising the steps of:
    a) providing control fluid to said valve by placing a fluid source in fluid communication, through a pressure-inducing apparatus, with said control port of said valve;
    b) operating said pressure-inducing apparatus to urge a flow of said control fluid through said control port toward a said fluid restriction valve operably to generate a back-pressure in said control fluid causing actuation fluid to displace said seal member from a normally-open position to a first-closed position effective to occlude said drain path;
    c) further operating said pressure-inducing apparatus to urge a flow of timing fluid causing additional displacement of said seal member effective to create a timing volume;
    d) stopping operation of said pressure-inducing apparatus; and
    e) waiting during a time-delay while said timing volume is permitted to drain through a bleed-down port to permit said seal member to return to a valve-open position.

13. The method according to claim 12 wherein said valve is included in an assembly adapted to periodically measure the bladder pressure in a medical patient to infer the abdominal pressure in that patient, the method further comprising the steps of:
    i) installing a urinary catheter in said patient to provide fluid communication between said bladder and a discharge portion of said catheter;
    ii) disposing an entrance port of said valve in fluid communication with said discharge portion so that said valve can provide a drain orientation and a measure orientation, said drain orientation permitting fluid flow from said entrance port through said valve and along said drain path toward a receptacle, said measure orientation providing fluid communication between said entrance port and said control port while said drain path is occluded;
    iii) disposing a pressure transducer in-circuit effective to measure the pressure of fluid in said bladder;
    iv) operating said pressure-inducing apparatus to place said valve into said measure orientation and to introduce a bolus of control fluid into said bladder; and
    v) using said pressure transducer to measure a hydrostatic pressure of the fluid in said bladder during said time-delay.

* * * * *

UNITED STATES PATENT AND TRADEMARK OFFICE
CERTIFICATE OF CORRECTION

PATENT NO. : 7,644,722 B2
APPLICATION NO. : 11/199790
DATED : January 12, 2010
INVENTOR(S) : Christensen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 913 days.

Signed and Sealed this

Sixteenth Day of November, 2010

David J. Kappos
*Director of the United States Patent and Trademark Office*